United States Patent [19]

Brey et al.

[11] Patent Number: 5,919,663
[45] Date of Patent: Jul. 6, 1999

[54] STABLE PURA VECTORS AND USES THEREFOR

[75] Inventors: Robert N. Brey, Rochester; James P. Fulginiti, Canandaigua; Algis Anilionis, Pittsford, all of N.Y.

[73] Assignee: American Cyanamid Company, Madison, N.J.

[21] Appl. No.: 08/380,297

[22] Filed: Jan. 30, 1995

Related U.S. Application Data

[63] Continuation of application No. 08/204,903, Mar. 2, 1994, abandoned, which is a continuation of application No. 07/695,706, May 3, 1991, abandoned.

[51] Int. Cl.$^6$ ............... C12P 21/02; C12N 15/63; C12N 1/21; C07H 21/04
[52] U.S. Cl. ............... 435/69.3; 435/172.3; 435/252.3; 435/252.33; 435/320.1; 536/23.1
[58] Field of Search ............... 435/69.3, 172.1, 435/172.3, 252.3, 252.33, 320.1; 530/350; 536/23.1

[56] References Cited

U.S. PATENT DOCUMENTS

| | | | |
|---|---|---|---|
| 4,550,081 | 10/1985 | Stocker | 435/252.3 |
| 4,735,801 | 4/1988 | Stocker | 424/235.1 |
| 4,760,022 | 7/1988 | Molin et al. | 435/69.1 |
| 4,837,151 | 6/1989 | Stocker | 424/200.1 |

FOREIGN PATENT DOCUMENTS

| | | |
|---|---|---|
| 0184086 | 6/1986 | European Pat. Off. . |
| 0251579 | 1/1988 | European Pat. Off. . |
| 0258118 | 3/1988 | European Pat. Off. . |
| 0286303 | 10/1988 | European Pat. Off. . |
| 0322237 | 6/1989 | European Pat. Off. . |
| 89/02924 | 4/1989 | WIPO . |
| 90/12086 | 10/1990 | WIPO . |
| 92/11361 | 7/1992 | WIPO . |

OTHER PUBLICATIONS

Davis et al. Microbiology Harper and Row, Publishers 357–358, 1973.
Wolfe and Smith, "Nucleotide Sequence and Analysis of the purA Gene Encoding Adenylosuccinate Synthetase of Escherichia coli K12", *J. Biol. Chem.* 263:19147–19153 (1988).
Abstract of Small Business Innovation Research Program Grant Proposal, Department of Health and Human Services, Grant No. R43 AI 26995–01.
O'Callaghan, D. et al., *Infection and Immunity* 56:419–423 (Feb. 1988).
Nakayama, K. et al., "Construction of an ASD$^+$ Expression–Cloning Vector: Stable Maintenance and High Level Expression of Cloned Genes in a Salmonella Vaccine Strain", *Bio/Technology* 6:693–697 (Jun. 1988).
Miwa, K. et al., *Gene* 31:275–277 (1984).
Gerdes, K., *Bio/Technology* 6:1402–1405 (Dec. 1988).
Niki, H. et al., *J. Bacteriol.* 170:5272–5278 (Nov. 1988).
Austin, S. et al., *J. Bacteriol.* 168:1010–1013 (Nov. 1986).
J. Hackett, "Salmonella–based Vaccines", *Vaccine* 8:5–11 (1990).
M.M. Levine et al., "Safety, Infectivity, Immunogenicity, and In Vivo Stability of Two Attenuated Auxotrophic Mutant Strains of Salmonella Typhi, 541Ty and 543Ty, as Live Oral Vaccines in Humans", *The Journal of Clinical Investigation* 79:888–902 (1987).
Nilsson et al., "Stabilization of Escherichia Coli Tryptophan–Production Vectors in Continuous Cultures: A Comparison of Three Different Systems", *Bio/Technology* 4:901–903 (1986).
Bass et al., "Overproduction, Purification, and Characterization of Adenylosuccinate Synthase from *E coli*," *Arch. of Biochem. and Biophy.* 256:335–342 (1987).
Sigwart et al., "Effect of a purA Mutation on Efficacy of Salmonella Live Vaccine Vectors," *Infection and Immunity* 57 (6):1858–1861 (1989).
Deich et al. Cloning of genes encoding a 15,000–dalton peptidoglycan–associated outer membrane lipoprotein and an antigenically related 15,000–dalton protein from Haemophilus influenzae J. Bacteriol. vol. 170 489–498, 1988.
Reznikoff et al. E. coli promoters pp. 1–33 in Maximizing Gene Expression Reznikoff and Gold, Eds. Buttterworths, Boston, 1986.

*Primary Examiner*—James Ketter
*Assistant Examiner*—John S. Brusca
*Attorney, Agent, or Firm*—Hamilton, Brook, Smith & Reynolds,P.C.

[57] ABSTRACT

This invention pertains to a complementation system for the selection and maintenance of expressed genes in bacterial hosts. The invention provides stable vectors which can be selected and maintained by complementation of chromosomal deletion mutations of purA (adenylosuccinate synthetase), obviating the use of antibiotic resistance genes. This system is useful in production organisms during fermentation and in live vaccine bacteria, such as attenuated *Salmonella typhi*. This system allows for selection of chromosomal integrants and for selection and stable plasmid maintenance in the vaccinated host without application of external selection pressure.

41 Claims, 9 Drawing Sheets

5,919,663

STABLE PURA VECTORS AND USES THEREFOR

This application is a continuation of application Ser. No. 08/204,903 filed Mar. 2, 1994, now abandoned, which is File Wrapper Continuation application of Ser. No. 07/695,706, filed May 3, 1991 (abandoned).

GOVERNMENT SUPPORT

Work described herein was supported in part by grant R43 AI 26995-01 from the National Institutes of Health. The government has certain rights in the invention.

BACKGROUND OF THE INVENTION

Plasmids found in nature are distributed to dividing cells so that daughter cells receive at least one copy. Bacterial plasmid systems utilize varying strategies to ensure correct partitioning of plasmids to progeny cells. Maintaining plasmids at high copy number increases the probability that daughter cells inherit at least one plasmid by random distribution so that the probability of progeny cells inheriting no plasmids is extremely low. Although random distribution systems theoretically can function to partition plasmids to dividing cells, plasmids which are maintained at unit or low copy number per cell must rely on active partition mechanisms. For example, plasmids which are maintained at low copy or one copy per cell such as the E. coli F factor (incF1), plasmid prophage P1(incY) and R1 and NR1 (incF2), must utilize active partitioning systems to maintain plasmids in the dividing cell population, since random distribution of plasmid would predict a loss rate of 25% per generation. Further, some higher copy number plasmids rely on site specific recombinases to resolve multimer formation, which functionally reduce the copy number of plasmids in cells and their ability to randomly partition by free diffusion.

Several active partitioning systems have been described for several families of bacterial plasmids. These systems share some common features. Plasmid replication functions can usually be assigned to distinct regions of plasmids. Plasmid replication regions (rep) of, for example P1 or F, can be independently maintained in cells. However, miniF or miniP1 plasmids lacking partition regions are unstable and are lost from the population at frequencies predicted from random distribution.

The development of plasmid vectors for the bacterial expression of heterologous genes for commercial purposes has been extensively documented. Numerous cloning vehicles based on various plasmid replicons have been described and used for production of proteins in E. coli and other bacteria. In the development of cloning vehicles suitable for expression of foreign proteins, the usual strategy has been to design plasmids of low molecular weight with high or regulated copy number. These strategies have sometimes led to the elimination of partition functions which would otherwise lead to stable plasmid inheritance. High copy number cloning vectors for the construction of production organisms often show segregational instability.

The most common strategy for obtaining stable plasmid replication and inheritance in the host population in fermentation has been the inclusion of drug-resistance determinants on the cloning vehicle. Although addition of drugs to growth medium allows selection for cells containing plasmid, addition of antibiotics is unacceptable in many instances because of cost and possible contamination of the end product.

Several alternate strategies have been developed to achieve stable plasmid maintenance during fermentation. For example, the parB locus of R1 has been subcloned into a variety of plasmid common cloning vectors. Resulting plasmids containing the R1 parB region showed enhanced stability when cultured in the absence of selective pressure. Likewise, the sop region of F can stabilize unstable oriC plasmids and P1 par can stabilize a mini-F plasmid that lacks its own partition functions. The stability of cloning vectors containing tryptophan operon genes was increased by addition of the par locus of pSC101 and the unstable multicopy vector derived from p15a (pACYC184) was stabilized by the pSC101 par locus. Other partition regions, such as a partition region from a *Salmonella typhimurium* virulence plasmid, have also been used successfully to stabilize cloning vehicles.

Although cloning vehicles can essentially be stabilized by the addition of partition regions from stable plasmids, drug resistance determinants are still commonly used during fermentation. Drug-resistance markers are convenient for introduction of plasmids into host bacterial cells. Alternatively, plasmids can be introduced into recipient bacterial cells by complementation of host chromosomal mutations by plasmid-borne genes. Complementation systems rely on the construction of particular host chromosomal mutations, but can be used reliably to circumvent the inclusion of antibiotics to the culture medium. For example, complementation of nutritional defects can lead to plasmid stabilization. Complementation of a chromosomal mutation for aspartic semialdehyde dehydrogenase (asd) in *Salmonella typhimurium* or D-alanine racemase mutation (dal) in *Bacillus subtilis*, which each lead to faulty cell wall biosynthesis and cell lysis, yields stable plasmid inheritance in the absence of selection in all viable cells of the culture. Both the asd and dal mutations can be phenotypically repaired by supplementation with nutritional additives. On the other hand, complementation of an essential gene of the host, which defect cannot be overcome by nutritional supplementation can also stabilize plasmids. For example, an E. coli gene, ssb, is required for DNA replication and cell viability and prevents the accumulation of plasmidless cells during fermentation in a bioreactor when incorporated into a plasmid and can be used to complement a chromosomal ssb defect. Analogously, a plasmid borne copy of valyl tRNA synthetase stabilizes plasmids in E. coli containing a chromosomal temperature-sensitive valyl tRNA synthetase. Plasmids can also be stabilized by inclusion of a bacteriophage repressor gene, the loss of which leads to induction of host prophage and cell death.

SUMMARY OF THE INVENTION

A stable plasmid or bacteriophage vector system for selection and maintenance has been developed for bacteria that can produce heterologous gene products during fermentation, or for use in segregational stabilization of antigen production in live attenuated bacterial vaccines. This system relies on the complementation of a chromosomal deletion mutation by expression of a functional gene for adenylosuccinate synthetase (purA gene product).

Three methods can be used to provide functional purA gene product (adenylosuccinate synthetase) for selection and maintenance. First, a low copy-number plasmid can be used as the vector from which expression of the purA gene is sufficient to complement the chromosomal purA defect without overburdening the cell with an overabundance of the purA protein product. A second method is to provide the purA gene on a high copy-number plasmid from which it is inefficiently expressed. This can be achieved by any of a variety of methods well known in the art for down regulating gene expression, including site directed mutagenesis of the promoter or ribosome binding sequences to reduce the efficiency of transcription and hence expression of the purA gene. A third method is to provide a functional purA gene on an integrating vector, such as a plasmid or bacteriophage unable to replicate within the recipient purA host, and thus selecting for integration of the purA vector.

This system obviates the need to select bacterial transformants by antibiotic resistance and, for application to live bacterial vaccine vectors, prevents the release of drug-resistance genes into the environment and distribution to other gut flora by known genetic mechanisms. This invention is particularly useful in selection and maintenance of plasmids or integrating vectors in live attenuated bacterial vaccine strains, both in the growth and vaccine production and in antigen delivery phases in the vaccinated host.

DETAILED DESCRIPTION OF THE INVENTION

Figure 1:
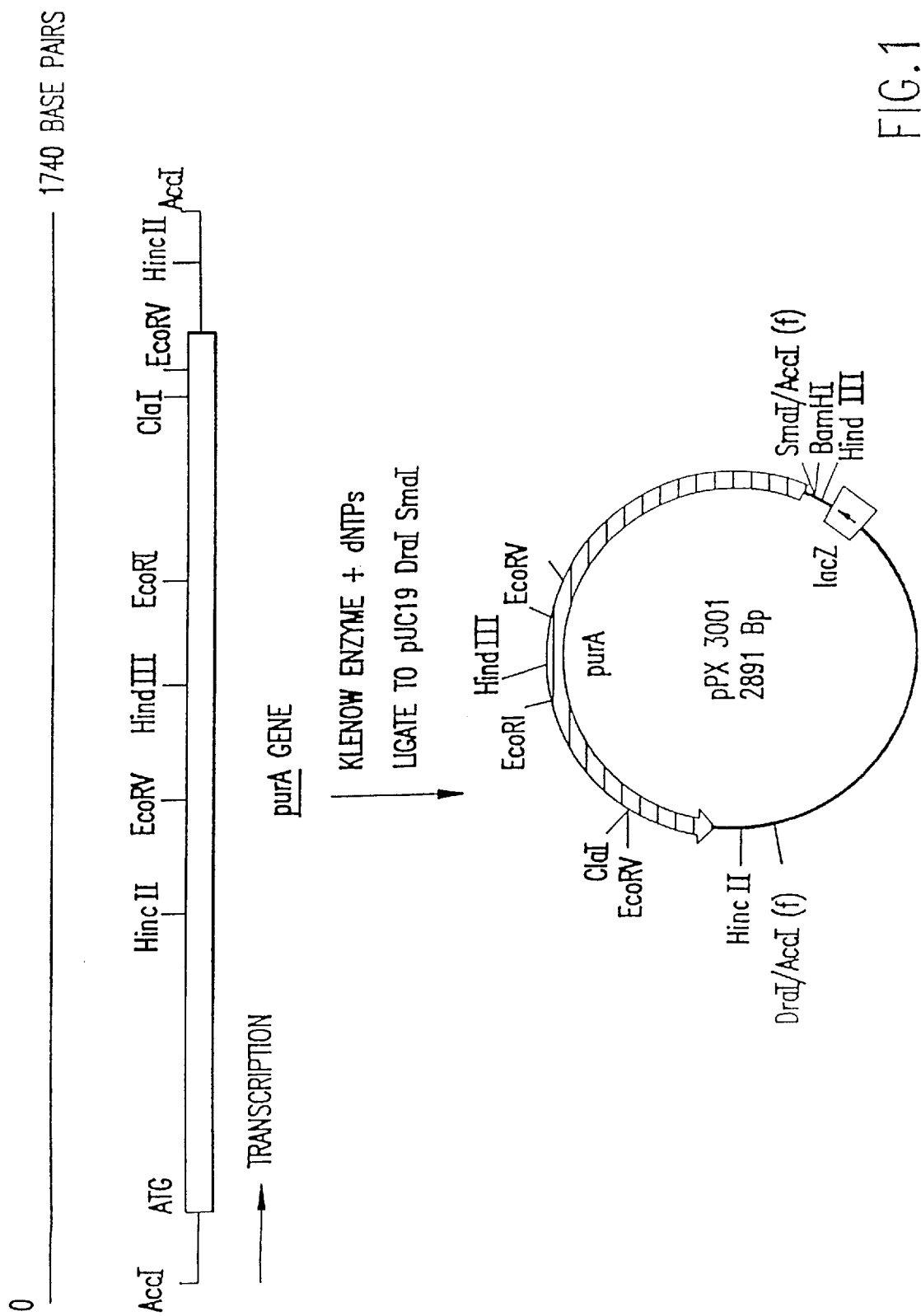
FIG. 1 shows the construction of plasmid, pPX3001, containing the E. coli purA gene under the control of the lacZ promoter.

Stable plasmid vectors for the complementation of chromosomal deletion mutations in the purA locus are described. These vectors can be used as a means for selecting clones carrying non-selectable markers or other passenger genes during clone construction. The vectors of this invention can also be used for maintaining these clones during growth for culture amplification, vaccine strain production, and gene product isolation.

Stable purA vectors of the invention provide a functional purA gene which is capable of expressing adenylosuccinate synthetase, repairing any defect in purine biosynthesis and allowing growth. In contrast, in strains with a defective purA gene, purine requirements can only be satisfied by nutritional supplementation with extracellular adenine or adenosine. Thus, growth of cells carrying the purA vector, in adenine-deficient medium ensures the continued selection and maintenance of the plasmid vector. Deletions of the host purA gene are preferred as these mutations do not revert. Extensive deletions are more preferable because these eliminate extensive homology between plasmid purA and chromosome, which could lead to chromosomal integration of the plasmid and to marker rescue of the purA gene in a double crossover event with concomitant loss of the expressed passenger gene. Use of a complementing purA gene from a heterologous bacterial source reduces the frequency of these possible undesired homologous recombination events.

This system relies on the complementation of a chromosomal deletion mutation by expression of a functional gene for adenylosuccinate synthetase (purA gene product). The purA locus is especially important in the design of live attenuated Salmonella and related enteric vaccine vectors since the presence of purA mutations on the chromosome leads to attenuation of virulence. In vivo, the presence of purA on a plasmid or bacteriophage vector which also codes for the expression of at least one polypeptide immunogen, prevents the appearance of organisms lacking immunogen expression within the vaccinated host. When combined with other attenuating loci, such as ones determining auxotrophic-requirements for aromatic compounds, purA leads to further attenuation of virulence. Chromosomal deletion of these genes leads to the impaired ability to replicate within the host, because of lack of availability of free purines (such as adenine or adenosine) or vitamin precursors (such as folic acid) which are dependent upon aromatic compound biosynthesis. Thus, Salmonella typhimurium harboring deletion mutations in both aroA and in purA are ineffective in inducing a significant immune response directed against the bacterium, whereas bacteria harboring solely defects in aromatic biosynthetic genes (such as aroA) are effective in inducing immune responses. Although Salmonella harboring aroA mutations are able to replicate to a limited extent intracellularly, those containing additional purA mutation are completely unable to replicate within the host. By providing the purA product of E. coli located on a plasmid to an aro purA host bacterium, the complemented vaccine has in vivo growth properties identical to those of the Aro-mutant.

Several general methods for selection and stabilization of expression are described herein using low copy-number plasmid vehicles, high copy-number plasmid vehicles, and vectors allowing recovery of single copy chromosomal integration events. In the case of low copy-number vectors, complementation of purA chromosomal defects can provide additional stability to plasmids also containing functional partition loci.

In the case of high copy-number vectors of this invention the purA gene is preferably mutated to reduce the efficiency of expression of the gene product and hence prevent growth inhibition by deleterious effects of an overabundance of the adenylosuccinate synthetase (purA) enzyme.

Construction of purA Plasmid Vectors

Recombinant DNA technology was employed in the construction of the purA plasmids. Recombinant techniques involve insertion of specific DNA sequences into a DNA vehicle (vector) to form a recombinant DNA molecule which is capable of replication in a host cell. The inserted DNA sequence may be foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules.

Regardless of the method used for construction, the recombinant DNA molecule must be compatible with the host cell, i.e., capable of autonomous replication in the host cell or stably integrated into one or more of the host cell's chromosomes or plasmids. The recombinant DNA molecule should preferably also have a marker function which allows the selection of the desired recombinant DNA molecule(s). In addition, if all of the proper replication, transcription, and translation signals are correctly arranged on the recombinant vector, the foreign gene will be properly expressed in, e.g., the transformed bacterial cells, in the case of bacterial expression plasmids, or in permissive cell lines or hosts infected with a recombinant virus or carrying a recombinant plasmid having the appropriate origin of replication.

Different genetic signals and processing events control levels of transcription and such as DNA transcription and messenger RNA (mRNA) translation. Transcription of DNA is dependent upon the presence of a promoter, which is a DNA sequence that directs the binding of RNA polymerase and thereby promotes mRNA synthesis. The DNA sequence of eucaryotic promoters differs from those of procaryotic promoters. Furthermore, eucaryotic promoters and accompanying genetic signals may not be recognized in or may not function in a procaryotic system, and furthermore, procaryotic promoters are not recognized and do not function in eucaryotic cells.

Similarly, translation of mRNA in procaryotes depends upon the presence of the proper procaryotic signals, which differ from those of eucaryotes. Efficient translation of mRNA in procaryotes requires a ribosome binding site called the Shine-Dalgarno (S/D) sequence (J. Shine and L. Dalgarno, *Nature*, 254:34–38 (1975)) on the mRNA. This sequence is a short nucleotide sequence of mRNA that is located before the start codon, usually AUG, which encodes the amino-terminal (formyl-) methionine of the protein. The S/D sequences are complementary to the 3' end of the 16S rRNA (ribosomal RNA), and probably promote binding of mRNA to ribosomes by duplexing with the rRNA to allow correct positioning of the ribosome.

Successful expression of a cloned gene requires sufficient transcription of DNA, translation of the mRNA, and in some instances, post-translational modification of the protein. Expression vectors have been used to express genes under the control of an active promoter in a suitable host, and to increase protein production.

Various regulatory expression elements can be used, which are any of a number of suitable transcription and translation elements that are active in bacteria. For instance, promoters which may be used to direct the expression of the recombinant gene sequence include but are not limited to the lactose operon promoter of *E. coli*, the hybrid trp-lac UV-5 promoter (tac) (H. DeBoer, et al., *In Promoter Structure and Function*, (1982); R. L. Rodriguez and M. J. Chamberlain, eds., Praeger Publishing, New York), the leftward (PL) and the rightward (PR) promoters of bacteriophage lambda, bacteriophage T7 promoters, the trp operon promoter, the 1pp promoter (*E. coli* lipoprotein gene promoter; K. Nakamura and I. Inouye, *Cell*, 18:1109–1117 (1979), etc. Other promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the native gene sequences encoding its own initiation codon and adjacent sequences are inserted into the appropriate expression vectors, no additional translational control signals may be needed. However, in cases where the native translational signals are not present, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Methods for constructing the appropriate expression vectors may include in vitro recombinant DNA and synthetic techniques and in vivo recombinations (genetic recombination).

For reviews on maximizing gene expression, see Roberts and Lauer, *Meth. Enzymol*, 68:473 (1979); and W. Reznikoff and M. Gold, Maximizing Gene Expression, Plenum Press, New York (1986).

U.S. Pat. No. 4,237,224 to Cohen and Boyer describes production of recombinant plasmids using processes of cleavage with restriction enzymes and joining with DNA ligase by known methods of ligation. These recombinant plasmids are then introduced by means of transformation and replicated in unicellular cultures including procaryotic organisms and eucaryotic cells grown in tissue culture.

Another method for introducing recombinant DNA molecules into unicellular organisms is described by Collins and Hohn in U.S. Pat. No. 4,304,863. This method utilizes a packaging/transduction system with bacteriophage vectors (cosmids).

The expression vector comprising the recombinant gene sequence should then be transferred into a bacterial host cell where it can replicate and be expressed or undergo conditional replication. This can be accomplished by any of numerous methods known in the art including but not limited to transformation (e.g., of isolated plasmid DNA into the attenuated bacterial host), phage transduction (Schmeiger, *Mol. Gen. Genetics*, 119:75 (1972)), conjugation between bacterial host species, electroporation, etc.

Expression in Attenuated Invasive Bacteria

In a preferred embodiment of the present invention, the expression vector comprising the purA gene is transferred into an attenuated invasive bacterium, where it is expressed, thus producing a bacterial strain suitable for use as a live vaccine.

Any of various attenuated invasive bacteria can be used as a vehicle to express the recombinant gene(s) so that the heterologous antigen is effectively presented to the host immune system, in the vaccine formulations of the present invention. The bacteria retain their invasive properties, but lose in large part their virulent properties, thus allowing them to multiply in the host to a limited extent, but not enough to cause significant disease or disorder. Examples of invasive bacteria which, in attenuated forms, may be used in the vaccine formulations of the invention include but are not limited to Salmonella spp., invasive *E. coli* (EIEC), and Shigella spp. In a preferred embodiment, invasive bacteria which reside in lymphoid tissues such as the spleen (e.g., Salmonella spp.) are used. Such bacteria can invade gut epithelial tissue and/or Peyer's patches, disseminate throughout the reticuloendothelial system, and gain access to mesenteric lymphoid tissue, liver and spleen, where they multiply or at least survive for a time, and induce humoral and cell-mediated immunity.

Attenuated invasive bacteria may be obtained by numerous methods including but not limited to chemical mutagenesis, genetic insertion, deletion (J. Miller, Experiments in Molecular Genetics, Cold Spring Harbor Laboratory, Cold Spring Harbor, N.Y.) or recombinant DNA methodology (T. Maniatis, et al., Molecular Cloning, A Laboratory Manual, Cold Spring Harbor Laboratory, Cold Spring Harbor, N.Y.), laboratory selection of natural mutations, etc. Methods for obtaining attenuated Salmonella strains which are non-reverting non-virulent auxotrophic mutants suitable for use as live vaccines are described in U.S. Pat. Nos. 4,550,081 (issued Oct. 29, 1985), 4,735,801 (issued on Apr. 5, 1988) and 4,837,151 (issued Jun. 6, 1989), the teachings of which are incorporated by reference herein in their entirety. A reliable method to achieve attenuation of Salmonella has also been described (S. K. Hoiseth, and B. A. D. Stocker, *Nature*, 291:238 (1981); B. A. D. Stocker et al., *Develop. Biol. Standard*, 53:47 (1982)) and can be used in a particular embodiment of the invention.

Attenuated Salmonella which can be used in the live vaccine formulations of the invention include but are not limited to those species listed in Table 1 below.

TABLE 1

SALMONELLA SPECIES WHICH, IN ATTENUATED FORMS, CAN BE USED IN THE VACCINE FORMULATIONS OF THE PRESENT INVENTION*

S. typhi
S. typhimurium
S. paratyphi A
S. paratyphi B
S. enteritidis
(e.g., Serotype dublin)

*For a complete description of Salmonella serotypes, see Edward and Ewing, 1986, Classification of the Enterobacteriaceae, 4th ed. Elsevier, N.Y.

In specific embodiments, Salmonella bacteria that have been attenutated by chromosomal deletion of gene(s) for aromatic compound biosyntheorsis (aro), or mutation in the galE gene, or that are Cya-, CrpF- or lack the Vir Plasmid, etc., can be used. Aro mutants which can be used include but are not limited to *S. typhi* strains 543Ty and 541Ty, for use in vaccines for humans, and *S. typhimurium* SL3261 and SL1479, and *S. enteriditis* serotype *dublin* SL1438, (also termed *S. dublin*) for use in animals. (See U.S. Pat. No. 4,550,081 for a description of *S. typhimurium* strains such as 543Ty and 541Ty are avirulent in humans by virtue of attenuation by deletion affecting genes aroA and/or purA (M. M. Levine, et al., *J. Clin. Invest.*, 79:888 (1987)). Mutants of *S. dublin*, such as SL1438, and of *S. typhimurium*, such as SL3261, can be used in the development of animal model systems, since these species are capable of causing animal diseases equivalent to typhoid fever. galE mutants which can be used include but are not limited to *Salmonella typhi* strains Ty21a (Germanier, Bacteria Vaccines, Academic Press, NY pp. 137–165) *Salmonella typhimurium* G30D, etc.

Expression of Gene Products and Uses

The invention also pertains to methods for introducing, selecting and maintaining single or multiple copies of homologous and/or heterologous genes, either in low copy-number plasmids, high copy-number plasmids or integrated in the host bacterial chromosome as single or multiple copies.

Expressible genes can be derived from eucaryotic sources and can encode antigenic determinants from pathogenic parasites, human immunoactive peptides and proteins, hormones, growth factors, allergens, tumor associated antigens and other proteins. Such genes can be derived from viral sources and can encode antigenic proteins, structural components or enzymes involved with viral replication or attachment. Homologous genes as well as heterologous genes can be derived from bacterial viral, parasite, fungal or mammalian sources and may include genes encoding virulence factors of pathogenic organisms, including toxins, protective immunogenic proteins or genes encoding proteins involved in the regulation or synthesis of antigenic polysaccharide material and, in addition, can be enzymes foreign to the host bacterium.

Among the bacterial antigens of interest are those associated with the human bacterial pathogens including *Haemophilus influenzae, Escherichia coli, Neisseria meningiditis, Streptococcus pneumoniae, Streptococcus pyogenes, Branhamella catarrhalis, Vibrio cholerae, Corynebacterium diphtheriae, Chlamydia trachomatis, Neisseria gonorrhea, Bordetella pertussis, Pseudomonas aeruginosa, Staphylococcus aureus, Klebsiella pneumoniae* and *Clostridium tetani*. Examples of specific bacterial antigens of interest include bacterial proteins of which particularly useful examples are outer membrane proteins (e.g., from *Haemophilus influenzae, Branhamella catarrhalis* or *Neisseria meningiditis*), bacterial toxins, (e.g., pertussis toxins, diphtheria toxin, tetanus toxin and Pseudomonas exotoxin A) and bacterial surface proteins (e.g., flagellins, hemagluttinins and the M protein from *Streptococcus pyogenes*).

Viral antigens from pathogenic viruses include but are not limited to human immunodeficiency virus (types I and II), human T cell leukemia virus (types I, II and III), respiratory syncytial virus, hepatitis A, hepatitis B, hepatitis C, non-A and non-B hepatitis viruses, herpes simplex virus (types I and II), cytomegalovirus, influenza virus, parainfluenza virus, poliovirus, rotavirus, coronavirus, rubella virus, measles virus, varicella virus, Epstein Barr virus, adenovirus, papilloma virus and yellow fever virus.

Several specific viral antigens of these pathogenic viruses include the F protein (especially antigens containing the F peptide 283–315, described in WO89/02935 entitled "Respiratory Syncytial Virus: Vaccines and Diagnostic Assays" by Paradiso, P. et al.) and the N and G proteins of respiratory syncytial virus (RSV), VP4 (previously known as VP3), VP6 and VP7 polypeptides of rotavirus, envelope glycoproteins of human immunodeficiency virus and the surface and presurface antigens of hepatitis B and herpes glycoproteins B and D.

Fungal antigen that can be used are those derived from fungi including but not limited to Candida spp. (especially *albicans*), Cryptococcus spp. (especially *neoformans*), Blastomyces spp. (e.g., *dermatitidis*), Histoplasma spp. (especially *capsulatum*), Coccidioides spp. (especially *immitis*), Paracoccidioides spp. (especially *brasiliensis*) and Aspergillus spp. Examples of parasite antigens include but are not limited to Plasmodium spp., Eimeria spp., Schistosoma spp., Trypanosoma spp., Babesia spp., Leishmania spp., Cryptosporidia spp., Toxoplasma spp. and Pneumocystis spp.

Also of interest are various antigens associated with auto-immune diseases, such as rheumatoid arthritis and lupus erythematosus, tumor antigens, cancer antigens and single and multiple copies of genes encoding hormones, bioactive peptides, cytokines, lymphokines and growth factors, as well as enzymes and structural proteins of procaryotic or eucaryotic origin, especially for use in vaccines or therapeutics.

To provide novel vaccine formulations, genes encoding protective antigens can be introduced into attenuated bacteria, which act as delivery vehicles for stimulation of immune responses against the pathogen from which the expressed gene was derived. See Dougan and Tite, *Seminars in Virology* 1:29 (1990). Genes encoding antigens derived from pathogenic bacterial, viral or parasitic sources can be introduced into attenuated *Salmonella typhi* for use as live vaccines in humans, to protect against, for example, typhoid fever, diarrheal diseases and sexually transmitted diseases including AIDS. Alternatively, such genes can be introduced into other Salmonella capable of infecting animal species, e.g., *S. dublin* for use as live attenuated cattle vaccines (e.g., against shipping fever or bovine rotavirus), *S. choleraesuis* for use as live attenuated vaccines for swine and *S. gallinarum* or *S. pullorum* for use as live attenuated vaccines for poultry. In a particular embodiment, antigens derived from *Eimeria* parasites can be introduced into attenuated *S. gallinarum* to produce an oral vaccine for coccidial disease.

Alternatively, genes encoding antigens can be introduced into other bacteria to be used as live vaccine delivery vehicles. Examples of such can include enteroinvasive *Escherichia coli, Yersinia enterocolitica, Shigella flexneri, Shigella dysenteriae, Campylobacter jejuni* and *Vibrio cholerae.*

In addition, such genes can be introduced into bacterial hosts to provide for efficient production of antigenic material for vaccine production. Expression of native or mutated genes derived from bacterial pathogens can result in enhanced and efficient antigen production. For example, genes encoding mutated toxins, genes encoding virulence factors or other native proteins or mutated protective immunogens can be introduced into homologous or heterologous bacterial strains. In many cases, virulence factors or protective antigens can be produced efficiently only in a particular host bacterium. In addition, genes which encode products involved in complex biosynthetic pathways leading to bacterial surface polysaccharide or capsule production cannot be readily cloned and expressed in other bacteria for the purpose of producing antigenic material for vaccine uses. Examples of such uses include introduction of genes encoding mutant cross-reacting toxins of *Bordetella pertussis* into toxin-deficient organisms for the production of a pertussis vaccine.

Bacteria harboring the stable purA plasmids of this invention can be used as live vaccines for eliciting an immune response to an immunogen in a warm-blooded animal. The method comprises administering the live vaccine to the animal such that the bacterium contained in the vaccine composition can express the immunogen in an immunologically effective dose capable of eliciting an immune response. The vaccines are useful for prevention of microbial infections. The vaccines may be administered in a pharmaceutically acceptable vehicle, such as physiological saline, or ethanol polyols (such as glycerol or propylene glycol).

The vaccines can be administered to a human or animal in a variety of ways. These include intradermal, transdermal, intramuscular, intraperitoneal, intravenous, subcutaneous, oral and intranasal routes of administration. The amount of live attenuated bacteria employed in such a vaccine will vary depending upon the identity of the antigen expressed. Adjustment and manipulation of established dosage ranges is well within the ability of those skilled in the art. The live vaccines of the present invention are intended for use in the treatment of both immature and adult warm-blooded animals, and in particular humans.

Typically, vaccination regimens call for the administration of antigen over a period of weeks or months in order to stimulate a "protective" immune response. A protective immune response, is an immune response sufficient to protect the immunized organism from productive infection by a particular pathogen or pathogens to which the vaccine is directed.

The invention will be further illustrated by the following exemplification which should not be construed as limiting the scope of the invention:

Exemplification

MATERIALS AND METHODS

Bacterial Strains and Plasmids

The bacterial strains and plasmids are described in Table 2 below.

TABLE 2

Strains used in development of stable expression plasmids for Salmonella vaccine strains

| species/strain designation | genotype |
|---|---|
| *Escherichia coli* | |
| JM103: | supE thi Δ(lac-proAB)hsdR4/F' [traDproAB$^+$laciq lacZm15 |
| TX595 | purA::mudlac T$^r$(amp$^r$) |
| TX595, λPB100 | purA::mudlac T$^r$ (amp$^r$) λPB100 (cm$^r$) |
| Salmonella species | |
| *S. typhimurium* | |
| SL5495 | zbj-908::Tn10 purAΔ155 |
| SL3261 | hisG46 aroADEL407 |
| SL3261 pur | hisGA6 aroADEL407 CRR[zbj-908::Tn10]Tc$^S$purAΔ155 |
| *S. dublin* | SVA47 aroAΔ148 CRR[zbj-908::Tn10]Tc$^S$ purAΔ155 |
| SL5653 | |
| *S. typhi* | |
| CDC10–80 | wild type |
| 679Ty | aroADEL148 |
| BB1333 | aroADEL148 aroDΔ9 |
| BB1354 | aroADEL148 aroDΔ9 CRR[zbj-908::Tn10]Tc$^S$purAΔ155 |

Media and Growth of Bacteria

Bacteria were grown in M9 medium supplemented with 0.5% casamino acids, 0.2% glucose, 0.02% $MgSO_4.7H_2O$, 5 μg/ml thiamine, 1 mM sodium citrate, 5 μg/ml nicotinic acid, 30 μg/ml each of phenylalanine, tyrosine and tryptophan, 10 μg/ml 2,3-dihydroxybenzoic acid, 10 μg/ml para-aminobenzoic acid and 1 μg/ml adenine. Plates contained 15 g agar per liter. Ampicillin was added at 100 μg/ml.

Genetic Transformation and Transduction

Plasmids were introduced directly into Salmonella by electroporation with a BTX Transfector 100 with the 0.5 mm electrode and a field strength of 15 kV/cm.

Plasmid constructions resulting from the ligation of synthetic oligonucleotides into plasmids were inserted into common laboratory strains of Escherichia coli by transformation (for details, see Maniatis et al., Molecular Cloning, A Laboratory Manual, Cold Spring Harbor Laboratory, Cold Spring Harbor, N.Y. (1982)). Plasmid constructions were isolated and characterized first in E. coli, before transferring to Salmonella spp., because of the high transformation frequencies of E. coli K-12 relative to those of S. typhimurium. Plasmids were transferred into S. typhimurium LT-2 LB5010, a strain which is restriction-negative (but modification-proficient) for the three restriction systems of Salmonella typhimurium, and also contains a mutation in galE resulting in higher transformation frequencies (for a description of restriction systems of Salmonella typhimurium, see Bullas et al., J. Bacteriol., 141:275 (1980)).

Plasmids were then inserted into attenuated Salmonella by transduction techniques. LB5010 containing the desired plasmid was grown in Luria broth (LB) to a density of $3 \times 10^8$ cells/ml, at which point D-galactose (to a final concentration of 1%) was added to the growth medium to induce synthesis of "smooth" lipopolysaccharide (LPS). Following 1.5 hours of growth in the presence of D-galactose, bacteriophage P22 HT 105/1 int was added to the culture to a multiplicity of infection of one. Following absorption of the phage, cells were immobilized in LB containing 0.7% agar. Phage were harvested and used to transduce plasmids into attenuated P22-sensitive Salmonella.

Electrotransfer Methods for Antigen Detection

Heterologous recombinant protein synthesis was detected in E. coli and Salmonella vaccine strain host cells by transblotting protein samples separated by polyacrylamide get electrophoresis onto nitrocellulose membranes, blocking with 1.5% Tween-20 in PBS, followed by antibody binding in 0.1% Tween-20. Bound antibody was detected with horseradish peroxidase labeled Protein A (Kirkegaard and Perry, Gaithersburg, Md). For detection of LT-B antigen, the primary antibody was goat α-LT-B polyclonal reagent, partially purified by eluting bound material from a Sepharose 4B protein A affinity column.

Restriction Enzyme Analysis

Horizontal gel electrophoresis of DNA was performed using standard methods (Maniatis, et al. "Molecular Cloning", Cold Spring Harbor, N.Y.). Restriction enzymes were purchased from Boehringer Mannhiem (Indianapolis, Ind.) and New England Biolabs Inc. (Beverly, Mass.).

In Vitro Stability Tests

Stability tests for plasmid-containing strains were carried out using dilutions of 1:1,000 from overnight cultures in M9 medium supplemented as described above. Dilutions were plated in duplicate on selective and non-selective media to determine plasmid retention. Additionally, colonies from non-selective plates were replicated using an FMC Repli-Plate (Rockland, Me.) onto selective plates to verify plasmid retention.

Immunization of Mice

Inocula were grown in M9 medium supplemented as described above to a density of $3 \times 10^8$ organisms/ml as determined by a Klett-Sommerson Colorimeter. Cells were pelleted at 5000 rpm for 15 min at 4° C. and resuspended in 1.5% (w/v) sodium bicarbonate to $2 \times 10^{10}$ organisms/ml (Klett 100) for intragastric (i.g.) inoculation and in phosphate buffered saline pH 7.2 to $1 \times 10^7$ organisms/ml for intravenous (i.v.) and intraperitoneal (i.p.) inoculation. Six week old BALB/c female mice were used routinely (Jackson Laboratories). Food and water were withheld for 4 hours prior to i.g. inoculation and returned 30 min post inoculation. $1 \times 10^{10}$ organisms/ml (0.5 ml inoculum) was administered i.g. using a Perfektum intubation needle (18G×2"). $1 \times 10^6$ organisms/ml (0.1 ml) was used for i.v. and i.p. inoculations.

Specimen Collection

Mice were sacrificed at various time points post inoculation. The liver, spleen and 3 Peyers patches were removed from each animal, placed in individual sterile bags and homogenized for 30 sec with a Stomacher Model 80 blender (A. J. Seward, London) using 5 ml of PBS (pH 7.2) for each liver sample and 2 ml for each spleen and Peyers patches sample.

Bacterial Colonization and Plasmid Stability

Organ homogenates were plated on selective and non-selective M9 medium supplemented as described above to determine plasmid retention. Colonies grown on non-selective plates were replicated onto SS agar (Difco, Detroit, Mich.) and onto selective plates to verify the percent of plasmid-containing colonies.

RESULTS

Complementation of purA auxotrophy in E. coli and Salmonella

The product of the purA gene, adenylosuccinate synthetase (EC 6.3.4.4) catalyzes the synthesis of adenylosuccinate from inosine monophosphate (IMP). This enzyme catalyzes the first committed step in the synthesis of adenine monophosphate (AMP) and is also involved in salvage pathways and the interconversion of nucleotides. Mutants of E. coli and other closely related enteric bacteria deficient in the structural gene for adenylosuccinate synthetase (purA) depend on exogenous adenine or adenosine, supplied nutritionally, for growth.

The gene for E. coli purA is contained within a 3.2 kilobase pair KpnI restriction enzyme fragment in plasmid pJS76 (Wolfe, S. A. and J. M Smith, "Nucleotide sequence and analysis of the purA gene encoding adenylosuccinate synthetase of Escherichia coli K12", J. Biol. Chem. 263:19147–19153 (1988)). For construction of plasmids which complement either E. coli or Salmonella purA auxotrophies, plasmid pJS76 (obtained from John M. Smith, Seattle Biomedical Research Institute), was used as a source of the E. coli purA gene product. Initially, the purA gene was inserted into pUC19 by ligating a blunt-end 1.75 kilobase pair AccI fragment with the DraI-SmaI fragment of pUC19, as diagrammed in FIG. 1. Plasmid pPX3001 was recovered in E. coli TX595 by selection for adenine-independent colonies. This initial construct, pPX3001, essentially retained the origin of replication of the starting pUC vector and replaced β-lactamase gene with purA, while at the same time retaining several useful cloning sites for further modification of the plasmid. This plasmid effectively complemented the purA gene defect in E. coli TX595 and resulted in a high copy-number plasmid phenotype characteristic of pUC plasmids.

Figure 2:
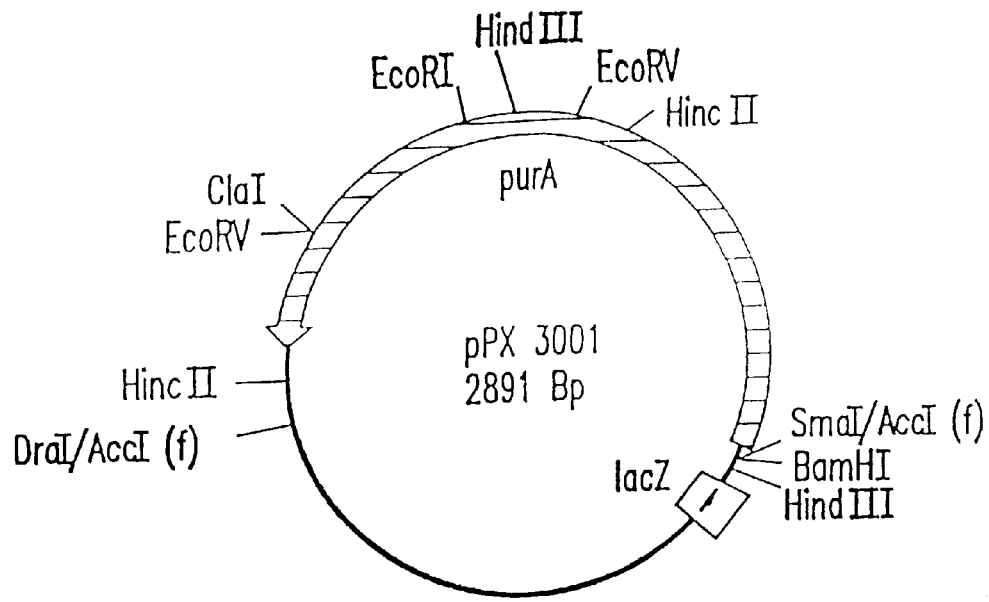
FIG. 2 shows the construction of plasmid pPX3003 containing the E. coli purA gene and the gene encoding the binding sub-unit of the heat-labile enterotoxin (LT-B) of E. coli, under the control of the lacZ promoter.
Figure 2:
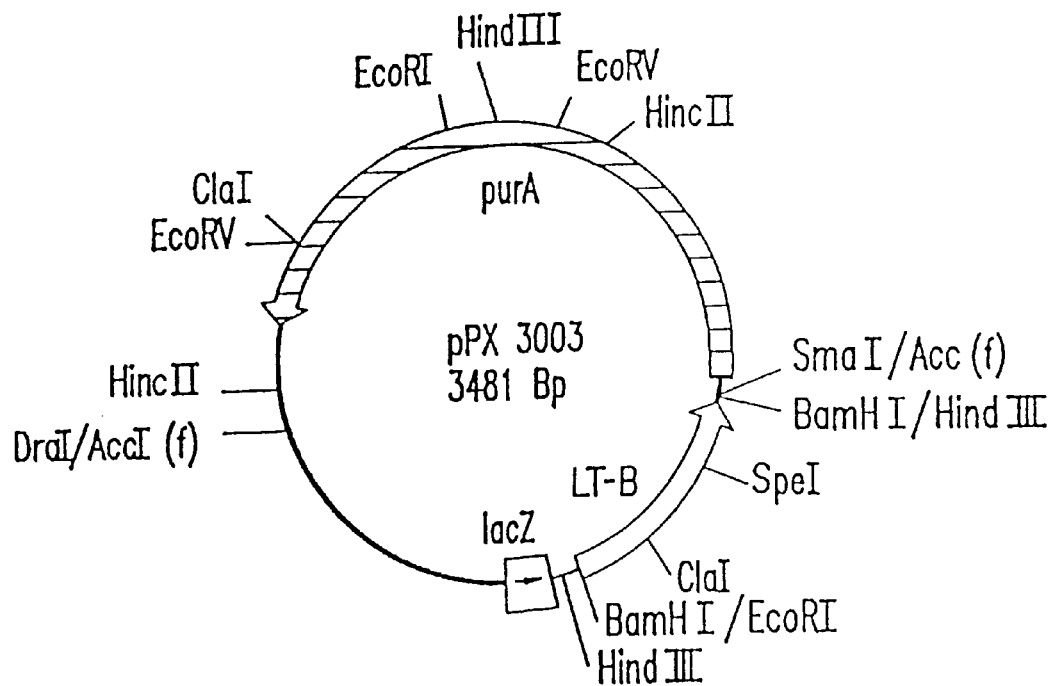

Plasmid pPX3001 was further modified to contain an additional expressed gene product. The gene for the atoxic subunit of enterotoxigenic E. coli labile toxin (LT-B) on a 600 base pair blunt-end EcoRI-HindIII was cloned into pPX3001, using a blunt-end BamHI site, as shown in FIG. 2. This plasmid construct, pPX3003, was recovered by transforming E. coli TX595 and selecting adenine-independent clones which expressed protein recognized on colony blots by polyclonal anti-LT-B antibodies.

Figure 3:
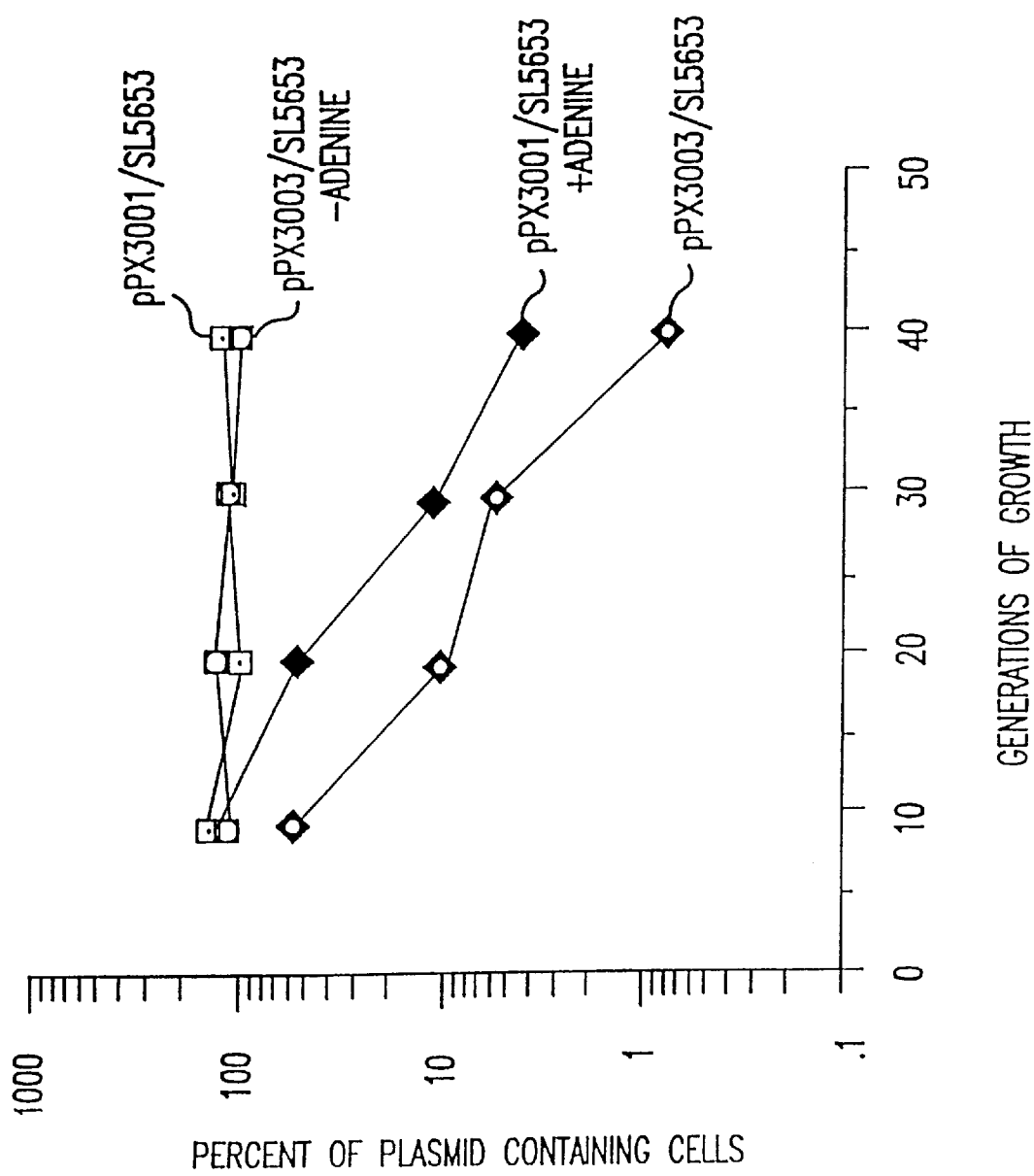
FIG. 3 is a graph of the percent of S. dublin SL5653 cells carrying the purA plasmids under selective (without added adenine) and non-selective conditions (with adenine added).
Figure 4A:
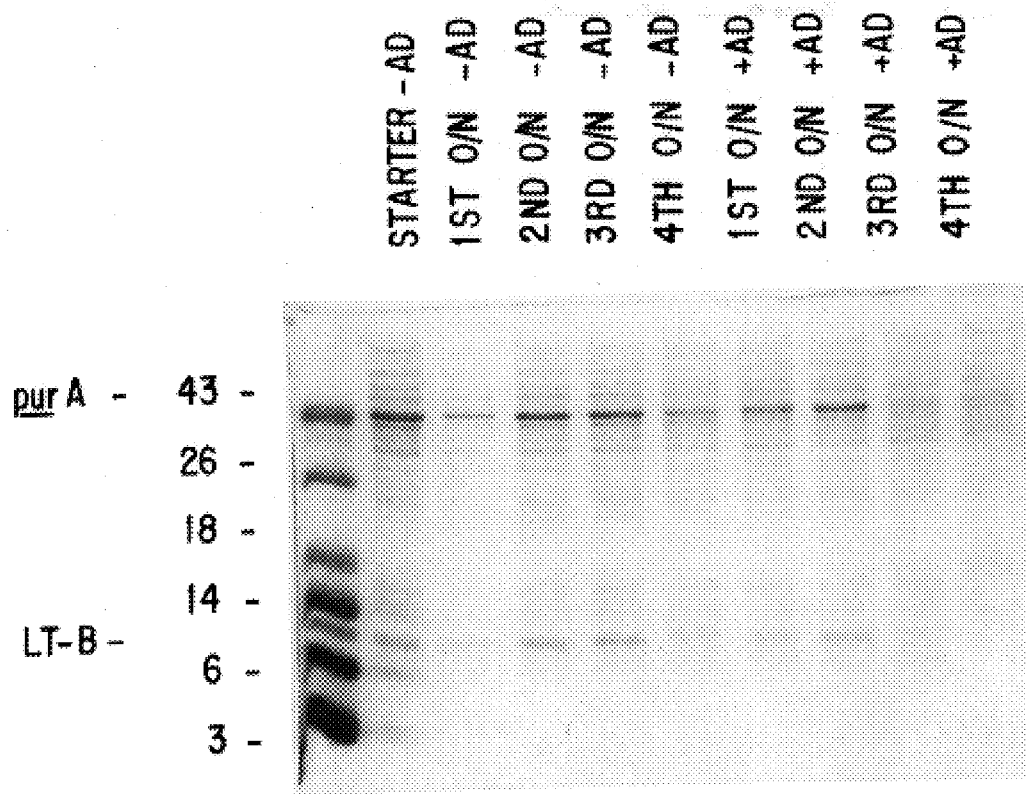
FIG. 4A shows an SDS polyacrylamide gel of total cellular protein from cultures of SL5653/pPX3003 grown in media containing adenine (+ad) or without adenine (–ad).
Figure 4B:
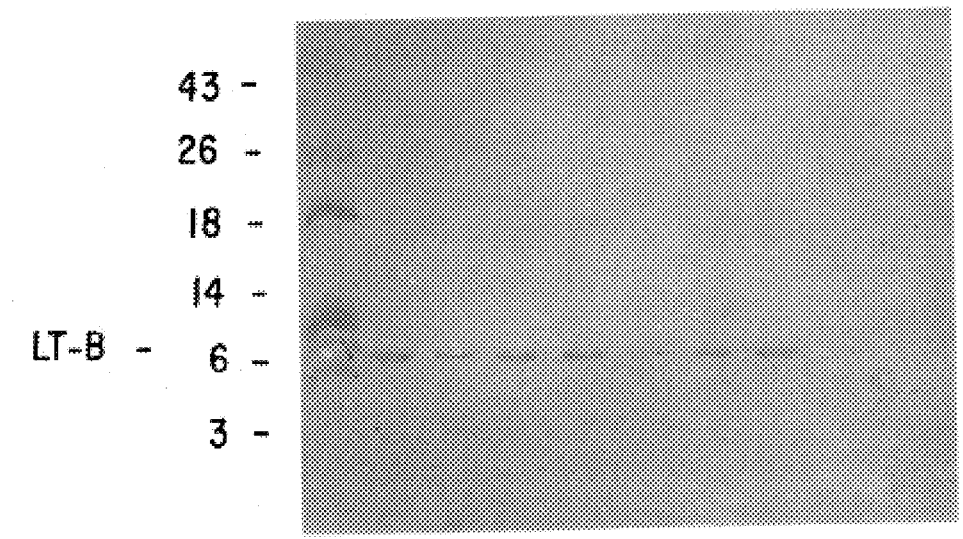
FIG. 4B shows a western blot of total cell proteins of SL5653/pPX3003 probed with goat anti-LT-B antiserum and visualised with HRP labeled protein A.
Figure 5:
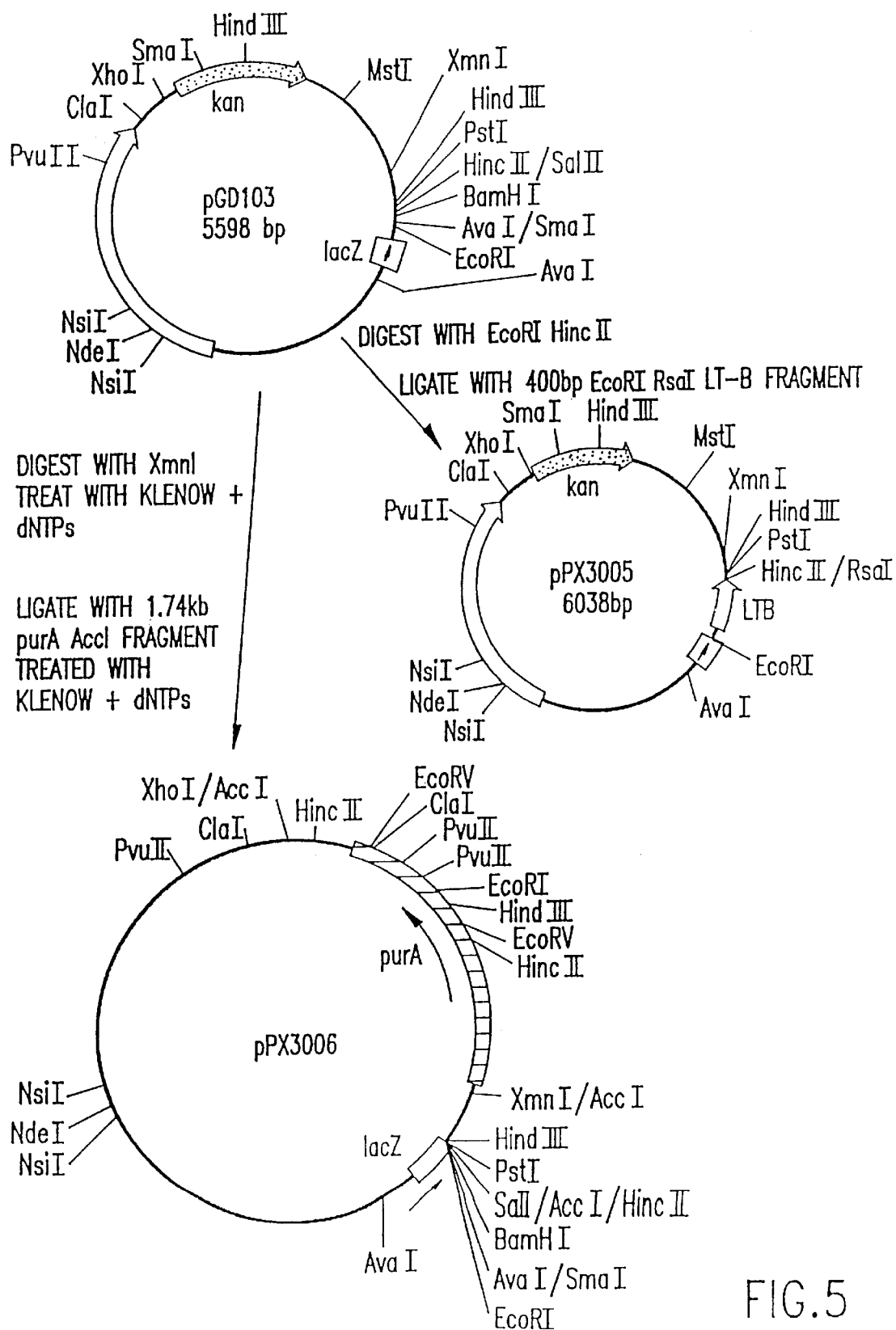
FIG. 5 shows the construction of two low copy-number plasmid vectors. Plasmid, pPX3005, contains the entire LT-B coding sequence and a Kanamycin-resistance determinant. Plasmid, pPX3006, contains the purA gene under the control of the lacZ promoter.

To examine stability of the purA vector, plasmid pPX3001, and the derivative LT-B expression plasmid pPX3003, were transformed into S. dublin SL5653 or into S. typhimurium BB1231, derivatives of Salmonella vaccine strains harboring deletion mutations in the purA gene. Salmonella transformants were examined for presence of the anticipated plasmids by DNA analysis, and in the case of pPX3003, for expression of LT-B. Suitable isolates of each strain were examined for retention of plasmid following passage in vitro under selective and non-selective conditions. As demonstrated in FIG. 3, plasmid containing colonies were initially grown under selective conditions, e.g., in defined medium lacking adenine, in overnight cultures. Samples in overnight cultures were washed and diluted into fresh medium either with or without adenine supplementation. After 10 generations of growth, cultures were transferred to similar fresh medium. At each 10 generation increment, samples were withdrawn from the cultures, diluted and plated onto either selective or non-selective agar medium. The proportion of colonies able to grow on unsupplemented media represents the portion of the culture population containing a purA-complementing plasmid. In unsupplemented medium, 100% of the colonies contain purA-complementing plasmids, whereas only a small percentage of resultant colonies from passage under adenine supplementation (non-selective conditions) contain plasmids after 40 generations of growth. Further, in cultures of SL5653 containing the LT-B expression plasmid pPX3003, LT-B expression and antigenicity is retained in the culture grown under selective conditions, but is lost under non-selective conditions. After 40 generations, each of the colonies from pPX3003/SL5653 grown under selective conditions arising on selective agar expresses LT-B, indicating no segregation of purA and LT-B expression. (See Table 3 and FIG. 4).

stabilize plasmids in the absence of exogenous adenine supplementation. Although purA complementation stabilized an LT-B expression plasmid in vitro, the particular plasmids, pPX3001 and pPX3003, are not likely to be optimally useful in a live Salmonella vaccine, since a combination of the purA and/or LT-B expression per se in the configuration above impedes the growth rate of the host Salmonella. In defined salts medium (M9) containing casamino acids, pPX3001/SL5653 and pPX3003/SL5653 had a doubling time of 1 hour, whereas SL5653 grown in the same medium supplemented with adenine had a doubling time of approximately 30 minutes. Although impairment of growth rate would result in further attenuation of the bacteria after oral feeding, it is also likely that decreased ability to establish a transient infection in the host animal would result in decreased immunogenicity. Thus, although plasmids are stabilized by complementation of chromosomal purA deletion, overexpression of the candidate antigen hyperattenuates the vaccine strain.

It is well known that the high copy-number pUC vector plasmids are stable in E. coli and Salmonella strains. The observed instability of the purA derivatives of the pUC plasmids is probably due to the expression of high levels of the purA gene product (seen as a 40Kdalton protein on SDS PAGE). The vectors of the present invention overcome this deleterious overexpression of the purA gene by one of two methods: First, by use of low copy-number plasmids to reduce the purA gene copy number and hence its expression; and second, by use of high copy-number plasmids carrying a purA gene which is inefficiently expressed.

Low Copy-Number Expression Plasmids and Integrated Expressed Genes

The above-results suggest that gene expression tailored to be neutral to the in vivo growth properties of a live Salmonella vaccine strain, combined with genetic stability, should yield a maximally immunogenic vaccine configuration. Appropriate levels of gene expression may be related inherently to the properties of the expressed antigen as well as the level to which it is expressed in the Salmonella vaccine strain. Several factors which may influence tolerance of the bacterial host strain to antigen expression include intracel-

TABLE 3

Maintenance of medium and high-copy number expression plasmids during culturing of Salmonella under selective and non-selective culture conditions

| Plasmid designation | derived from | marker/ expressed gene | host strain | Selection conditions | % plasmid containing colonies generations of growth[1] | | | | |
|---|---|---|---|---|---|---|---|---|---|
| | | | | | 10 | 20 | 30 | 40 | 80 |
| pUC8 | | Amp | SL3261 | +amp | 100 | 100 | 100 | 100 | 100 |
| | | | | −amp | 50 | 63 | 50 | 43 | n.d. |
| pPX100 | pUC8 | Amp/LT-B | SL3261 | +amp | 100 | 100 | 100 | 100 | 100 |
| | | | | −amp | 58 | n.d. | 71 | 41 | n.d. |
| pPX1601 | pBR322 | Amp/CS-LT-B | SL3261 | +amp | 100 | 100 | 100 | 100 | 100 |
| | | | | −amp | 100 | 100 | 85 | 54 | 33 |
| pPX3001 | pUC8 | purA | SL5653 | −ade | 100 | 100 | 100 | 100 | 100 |
| | | | | +ade | 92 | 46 | 11 | 4 | n.d. |
| pPX3003 | pUC8 | purA/LT-B | SL5653 | −ade | 100 | 100 | 100 | 100 | 100 |
| | | | | +ade | 48 | 10 | 6 | 1 | n.d. |

[1]plasmid content was assessed by enumerating colonies from culture dilutions on medium with and without selection;
n.d. = not determined These results indicate that the expressed purA gene carried on a high copy-number pUC plasmid functions to lular localization of the antigen, level of expression and stability of the antigen to proteolytic processing. Some of these factors may in turn be influenced by transcriptional and translational signals such as promoter strength, efficiency of ribosome recruitment and gene copy number.

To create a situation in which LT-B expression was stabilized by purA complementation and tailored to be neutral to the growth of a Salmonella vaccine strain, the effect of gene copy number on LT-B expression and tolerance by the Salmonella host was examined. This was examined under several conditions, one in which a lac promoter controlled LT-B was expressed on a low copy-number plasmid vector and one in which LT-B was expressed as a single chromosomal copy.

To construct a low copy-number LT-B expression plasmid, plasmid pGD103 (R. A. Deich et al.,(1988) *J. Bacteriol.* 170; 489–498), was digested with EcoRI and HincII and an EcoRI RsaI DNA fragment containing the entire LT-B coding sequence was cloned into the vector to yield pPX3005, an LT-B expressing plasmid also containing a kanamycin-resistance determinant. (See FIG. 5). Plasmid pPX3005 was transformed by electroporation into *S. typhimurium* SL3261. The growth of SL3261 harboring pPX3005 was compared with SL3261 containing the parental plasmid and with SL3261 proper. In M9 medium containing 0.5% casamino acids, no difference in growth rate was seen between the three strains, each with doubling times of approximately 45 minutes. This result suggested that the expression level of LT-B in this configuration was neutral to the growth properties of the host SL3261.

A chromosomal integrant of LT-B was obtained in the following manner: A plasmid containing a 31 base inverted repeat derived from the extreme ends of Tn10 and the expressed transposon gene of Tn10 under control of the tac promoter located outside the inverted repeat sequences was used to create a transposon which expressed LT-B. An 800 base pair HaeII restriction enzyme fragment, carrying the lac promoter region and the structural gene for LT-B was cloned into the transposon vector, also containing a kanamycin-resistance determinant. In this configuration, the gene for LT-B and kanamycin resistance were flanked by the inverted repeat sequences. To create a suicide vector for use in Salmonella strains, the transposon carrying LT-B and kanamycin was crossed into a derivative of λgt11 so that a hybrid phage particle carrying the LT-B transposon and the Tn10 transposase was constructed. A full explanation of this technique can be found in U.S. Ser. No. 07/590,364, filed Sep. 28, 1990, the teachings of which are incorporated herein by reference, and is similar to modified transposons described by Herrero et al., *J. Bacteriol*: 172: 6537–67 (1990). The modified λ phage carrying the LT-B transposon was used to infect Salmonella LB5010/F112, carrying an expressed λ phage receptor. Since DNA of phage λ does not replicate in Salmonella, clones selected for kanamycin-resistance result from transposition of the modified transposon onto the chromosome. Several independent isolates were obtained; all expressed the LT-B antigen. Several of the *S. typhimurium* LB5010 isolates were retained and P22 phage lysates propagated on them were used to transduce the chromosomally located expression cassette into the Salmonella vaccine strain SL3261. Two independent SL3261 LT-B chromosomal integrants, resulting from transduction from two separate alleles, located in different loci in the Salmonella chromosome, were found to be stable in vitro and in vivo.

Construction of a Low Copy-Number purA Vector

Plasmid pGD103 was modified to contain the *E. coli* purA gene and several unique cloning sites. The 1.7 kilobase pair AccI fragment of pJS76 was inserted into the XmnI XhoI sites of pGD103, to yield pPX3006. (See FIG. 5). In this plasmid, the kanamycin-resistance determinant was entirely replaced with purA, creating a vector with unique BamHI, SmaI, PstI and SalI sites.

Low Copy-Number purA Vector Containing PL Promoter Expression Cassettes

Plasmid pPX3006 was used as a vector to construct several low copy-number plasmids which expressed gene products under control of the strong λ PL promoter. It is expected that certain gene products whose transcription is regulated by the P1 promoter will be produced in the host bacterial cell at high levels compared with genes under control of weaker promoters such as the lac promoter. Further, because Salmonella strains are known not to be lysogenic for bacteriophage λ, expression of plasmid borne PL promoted proteins will be constitutive. Combined with stabilization by complementation of purA, such configurations will possibly overcome low levels of gene expression associated with low copy-number of the vector plasmid, pPX3006 and will enhance immunogenicity of live attenuated recombinant Salmonella strains.

Several versions of the *Plasmodium berghei* circumsporozoite protein (CS) gene were stabilized in pPX3006. The CS gene has been implicated as one of the major immunogens of the malaria sporozoite coat and, as such, is a candidate for a subunit approach for a malaria vaccine. The structures of several CS genes have been elucidated, revealing that all have a similar overall structure. The single outstanding feature of each is that they contain a central repeating peptide, comprising up to one third of the protein. The repeat regions are immunodominant, since the bulk of anti-sporozoite antibodies are directed against these regions. Although antibodies to the repeat regions have been implicated in protection against the sporozoite stage of malaria, antibodies alone are insufficient to achieve protection against sporozoite infection. It is likely that protection against sporozoite stage of malaria parasites involves not only a humoral response, but also a strong T-cell response. Most likely activation of cytotoxic T lymphocytes which recognize portions of the CS protein and other proteins of the developing sporozoite on the surface of sporozoite-infected hepatocytes is required for protection. Thus, vaccines designed to stimulate those responses specifically, or in conjunction with humoral responses, is necessary in effective malaria vaccines. Stimulation of cellular immunity at the level of cytotoxic T-cells can be achieved by delivering antigen to antigen presenting cells in a manner such that they are likely to be processed by an internal pathway of processing. Presentation of antigens via internal pathways may result preferentially in surface expression of antigen in association with class-I restricted MHC, usually associated with stimulation of CD8± cytotoxic T-cells. Expression of the CS protein of *P. berghei* and *P. falciparum* in attenuated Salmonella and subsequent oral immunization has resulted in induction of specific CD+ cytotoxic T-cells recognizing peptides of these CS proteins. Further, oral immunization of mice with *P. berghei* CS protein constructs resulted in significant protection against sporozoite challenge, usually only achieved by vaccination of animals with gamma-ray inactivated sporozoites.

Although protection against sporozoite challenge has been documented by vaccination with CS protein-expressing Salmonella, protection was incomplete, suggesting that adequate induction of immunity had not occurred. Further, this suggests that factors relating to CS protein expression in the attenuated Salmonella vaccine strain might be manipulated for enhanced immunogenicity. Such factors include, as mentioned above, gene regulatory signals, presumably affecting level of protein expression, stability of the expressed protein, and genetic stability of the expressed protein. If, during the course of the transient infection by the attenuated Salmonella, a significant proportion of the immunizing bacteria lose plasmid due to segregation, effective immunization will not occur.

Figure 6A:
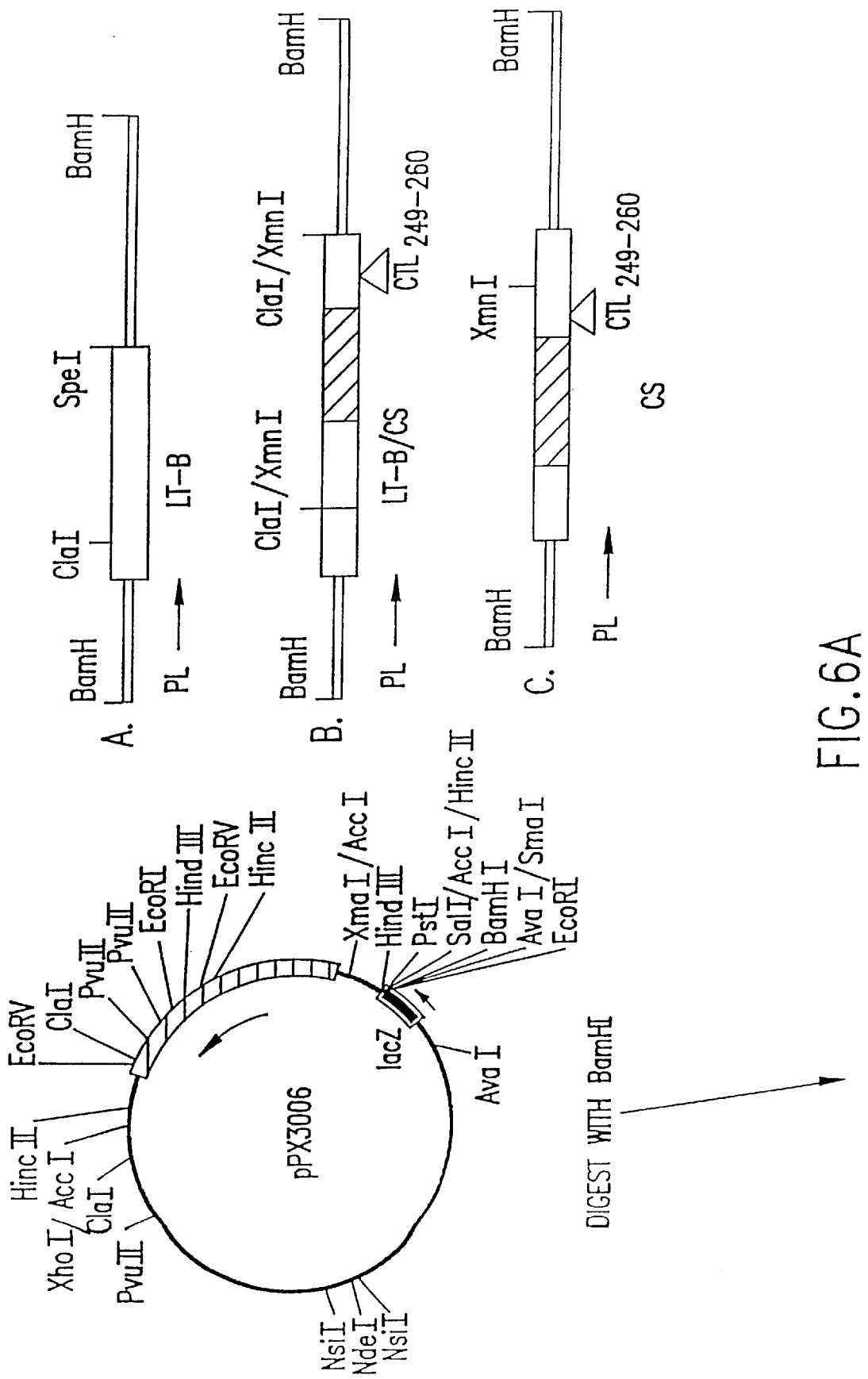
FIGS. 6A–6B show the construction of three purA plasmid vectors containing the coding sequence of LT-B (pPX3010), malarial circumsporozoite (CS) protein gene (pPX3009), and the nucleotide sequence encoding an LT-B/CS fusion protein (pPX3007).
Figure 6B:
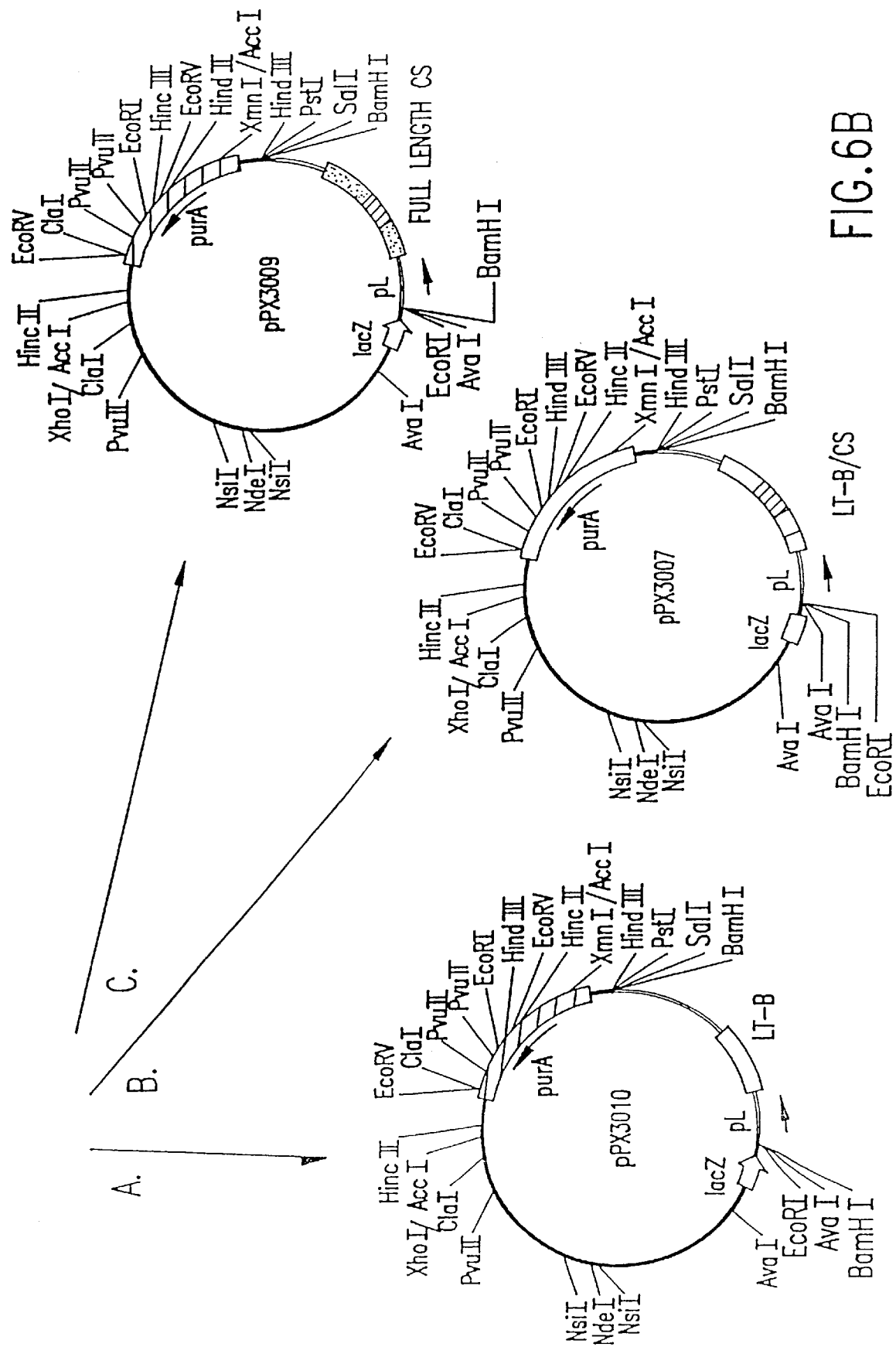

To evaluate the stabilization of CS protein constructs by complementation of purA, a full length CS protein construct was inserted into the BamHI site of pPX3006. This construct contains the entire coding sequence of the *P. berghei* (ANKA) CS protein gene expressed from the PL promoter and was designated pPX3009 (FIG. 6). A second construct containing a truncated CS protein (pPX1601) expressed from the P1 promoter as a fusion protein with the first 30 amino acids of LT-B was inserted into the BamHI site of pPX3006. This construct contains an LT-B fusion protein with an expressed portion of the CS protein lacking 60 amino acids of the amino terminus and 30 amino acids of the carboxy terminus. This construct was designated pPX3007 (FIG. 6). Both constructs were transformed into *S. typhimurium* BB1231 (ΔpurA), by selection for purine independence. When expression was compared to their cognate higher copy-number parental plasmids (derived from pBR322), no difference in levels of expression in SL3261 was seen, suggesting that gene expression was uncoupled from gene copy-number.

A third promoter controlled expression cassette was examined for stabilization by purA complementation. The coding sequence for LT-B (on a 590 base pair EcoRI-HindIII fragment, blunted by the action of Klenow enzyme) was inserted into the HpaI site of pPLλ (Pharmacia Molecular Biologicals, Piscataway, N.J.) to yield pPX1602. The coding sequence of LT-B, now located on a 1.7 kilobase pair BamHI fragment, was inserted into the BamHI site of pPX3006 to yield pPX3010 (FIG. 6). This plasmid was transformed into BB1231. Expression of LT-B antigen was compared at different points in the growth cycle of Salmonella and was compared between gene integrated forms, high copy-number plasmid forms and low copy-number plasmid forms. Maximum gene expression was seen in overnight cultures of the bacteria. Expression level was related to gene copy-number when expression of LT-B was controlled by the lac promoter. Expression was greatest in cultures containing pPX100, followed by pPX3005; with least expression being seen in cultures of SL3261λ3. However, expression of LT-B from pPX3010 exceeded that observed in cultures of pPX100, demonstrating that strong PL promoter had overcome gene copy-number effects for expression of LT-B antigen.

In Vitro Stability of Low Copy-Number and Chromosomal Integrant_Expression Cassettes

*S. typhimurium* SL3261 strains carrying expression cassettes on pBR322, pUC or pSC101 derivatives were compared for stability upon culturing in the absence of selection. As seen in Table 3, pUC vector plasmids or expression plasmids based on pUC plasmids, were drastically unstable upon culturing in vitro without ampicillin selection. Moreover, a plasmid (pPX1601) derived from pBR322 expressing a truncated *P. berghei* CS/LT-B fusion protein (described above) showed significant loss from passaged cultures in the absence of ampicillin.

When any of these expression cassettes was cloned into either pGD103 or its purA derivative (pPX3006), 100% retention of expression plasmids was observed for up to 80 generations. This result indicates that plasmids based on pSC101 replicon are inherently stable in *S. typhimurium*. Further, that purA gene of *E. coli* is effective in replacing drug-resistance determinants usually associated with cloning plasmids. (See Table 4).

TABLE 4

Maintenance of low-copy number expression plasmids containing parB during culturing of *Salmonella typhimurium* under selective and non-selective culture conditions

| Plasmid designation | derived from | marker/ expressed gene | host strain | Selection conditions | % plasmid containing colonies generations of growth[1] 10 | 20 | 30 | 40 | 80 |
|---|---|---|---|---|---|---|---|---|---|
| pGD103 | pSC101 | Kan | SL3261 | +kan | 100 | 100 | 100 | 100 | 100 |
| | | | | −kan | 100 | 100 | 100 | 100 | 100 |
| pPX3005 | pGD103 | Kan/LT-B | SL3261 | +kan | 100 | 100 | 100 | 100 | 100 |
| | | | | −kan | 100 | 100 | 100 | 100 | 100 |
| pPX3006 | pGD103 | purA/LT-B | SL3261pur | −ade | 100 | 100 | 100 | 100 | 100 |
| | | | | +ade | 100 | 100 | 100 | 100 | 100 |
| pPX3007 | pPX3006 | purA/LT-B CS | SL3261pur | −ade | 100 | 100 | 100 | 100 | 100 |
| | | | | +ade | 100 | 100 | 100 | 100 | 100 |
| pPX3009 | pPX3006 | purA/CS | SL3261pur | −ade | 100 | 100 | 100 | 100 | 100 |
| | | | | +ade | 100 | 100 | 100 | 100 | 100 |
| pPX3010 | pPX3006 | purA/LT-B | SL3261pur | −ade | 100 | 100 | 100 | 100 | 100 |
| | | | | +ade | 100 | 100 | 100 | 100 | 100 |

[1]plasmid content was assessed by enumerating colonies from culture dilutions on medium with and without selection;
n.d. = not determined Plasmid vectors containing the partitioning regions and functions associated with pSC101 are stable in *E. coli* and Salmonella under batch culture conditions. Although the par region of pSC101 is retained in pGD103 and the purA derivatives described here, partition functions alone may not be sufficient to allow effective plasmid stabilization during fermentation of the recombinant vaccine strains during production (Nilsson and Skogman 1986. *Biotechnology* 4:901–903). Plasmid complementation of a purA deletion mutation on the chromosome combined with retention of partition functions allows for efficient stability during batch growth, growth under nutrient-limiting conditions and during fermentation.

Figures 7A, 7B, 7C:
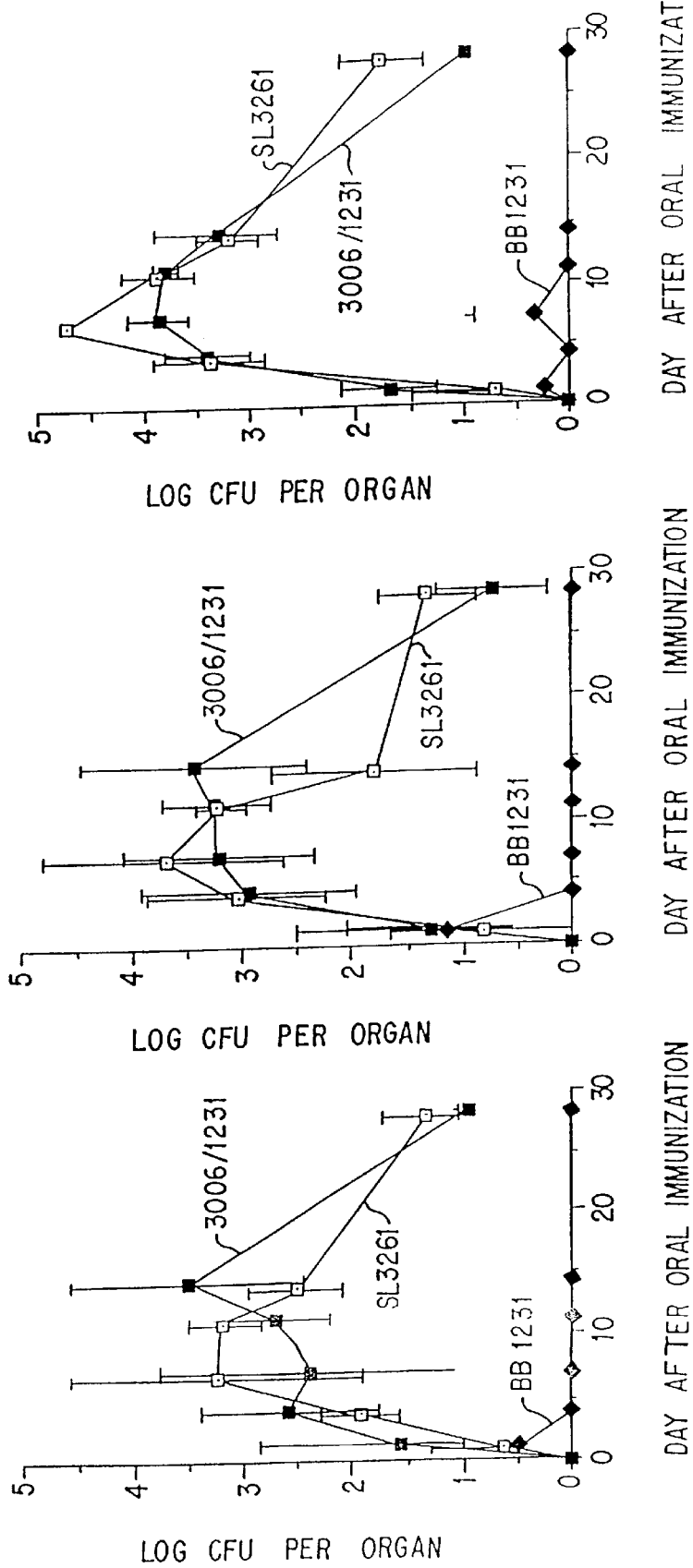
FIGS. 7A–7C shows the results of in vivo stabilization studies of Salmonella typhimurium strains by purA complementation. S. typhimurium recovered from A: spleens, B: livers and C: peyers patches.

In Vivo Stabilization of *Salmonella typhimurium* Vaccine Strains by purA Complementation To examine the stabilization of pSC101 plasmids by purA complementation under vaccination conditions, mice were immunized orally with SL3261, BB1231 (SL3261ΔpurA) and pPX3006/BB1231. Organ samples were obtained and examined for presence of the immunizing organisms up to 30 days following oral ingestion of the bacteria. As can be seen in FIGS. 7A–7C, BB1231 could be cultured from samples of spleen, liver and Peyer's Patches at very low levels only 2 days post inoculation, whereas, SL3261 and complemented BB1231 could be recovered in tissue samples for several weeks. The complemented vaccine strain yielded in vivo growth characteristics similar, if not identical within statistical variation, to SL3261. This indicates that purA complementation effectively restores the chromosomal purA deletion to pur+ behavior and is effectively neutral to invasion and bacterial replication properties of the vaccine strain.

Plasmids based on pSC101 are also stabilized in vivo. As shown in Table 5, in support of in vitro stability data, plasmids based on pSC101, whether additionally stabilized by purA complementation or not, are completely stable in organ samples obtained up to 29 days post inoculation. For those animals immunized with LT-B expression plasmids, all of the isolates characterized as containing plasmids also expressed the antigen. In contrast, a minority of organisms recovered from animals immunized with either pUC vector or pPX100 contained plasmid, so that no plasmid-containing organisms could be cultured from organ samples 15 days post inoculation. In addition, those animals receiving a gene integrated form of LT-B also showed 100% retention of expression (of kanamycin-resistance and LT-B).

ery of heterologous antigens to the human immune system. To demonstrate the utility of purA complementation in attenuated *S. typhi*, pPX3006 and pPX3010 were transformed by electroporation into an aroA *S. typhi* candidate BB1354 (679Ty ΔpurA). Presence of plasmid was verified and expression of LT-B in pPX3010 transformants was confirmed by western blot analysis. The two strains were examined for growth properties: doubling times for plasmid containing transformants were similar to untransformed parent. The two plasmid containing strains were examined for plasmid stability in vitro by passaging in the absence and presence of adenine. Both plasmids were 100% stable for up to 80 generations with and without selection.

Figure 8B:
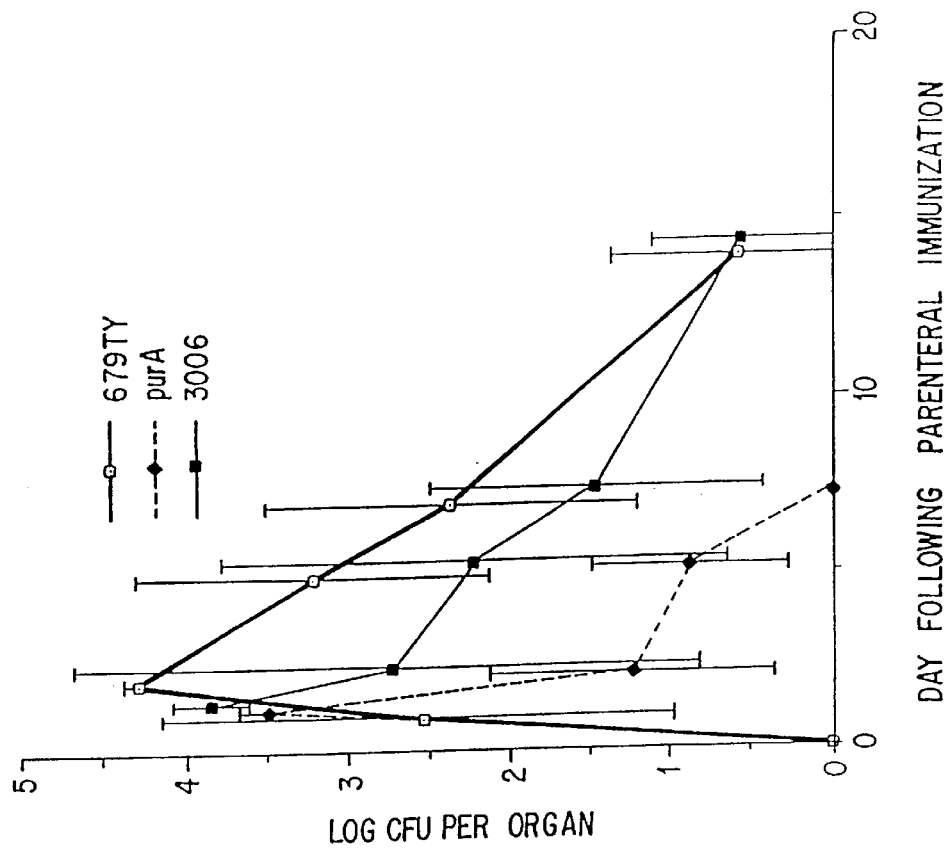
FIGS. 8A–8B shows the results of in vivo stabilization studies of S. typhi strains by purA complementation. S. typhi recovered from A: livers and B: spleens.
Figure 8A:
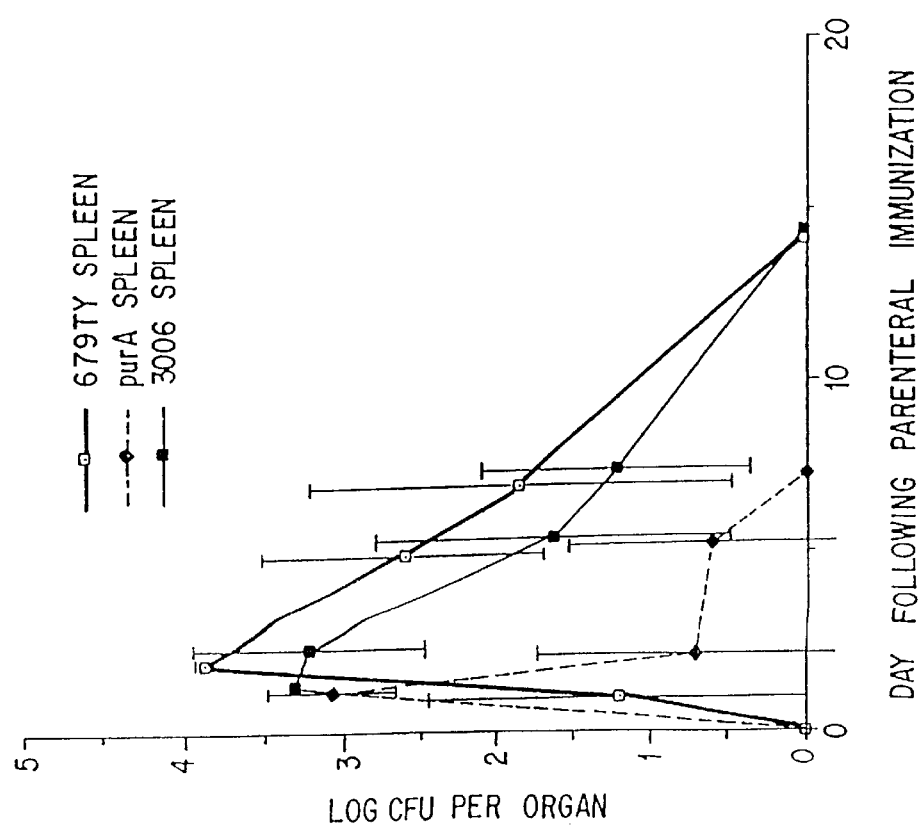

*S. typhi* strains 679Ty, BB1354 and pPX3006/BB1354 were compared for ability to persist within deep tissues following parenteral inoculation. *S. typhi* in its natural state is not a pathogen for mice and does not infect mice orally. When pPX3006/BB1354 or 679Ty ($10^7$ bacteria per animal) were used to inoculate mice, organisms were recovered from livers and spleens for up to 10 days following inoculation. On the other hand, BB1354 ($10^7$ organisms per animal) was recoverable only at very low levels for several days, demonstrating limited ability for these strains to grow in animal tissues. Further, complementation of the chromosomal purA deletion with purA gene on plasmid pPX3006 also complements ability of the deletion to persist in tissues. (See FIGS. 8A–8B).

The in vivo and in vitro results in *S. typhimurium* and *S. typhi* aroA purA strains clearly demonstrate the ability of plasmid-borne purA gene of *E. coli* to complement chromosomal defects in these strains. More significantly, complementation of the purA defect on a low copy-stable plasmid vector is neutral to the in vivo growth behavior of the vaccine bacteria. This strongly suggests that recombinant bacteria utilizing purA complementation should allow stable expression of heterologous antigens useful in oral inoculation.

TABLE 5

Persistence of plasmid-containing *S. typhimurium* aroA in Peyer's patches

| Immunizing bacteria, $10^9$ p.o. | Animal # | Day 10 | | | Day 15 | | | Day 29 | | |
|---|---|---|---|---|---|---|---|---|---|---|
| | | total | drugR | % with plasmid | total | drugR | % with plasmid | total | drugA | % with plasm |
| pUC8/S12261 (vector control) | #1 | 2 | 2 | 100 | 1 | 1 | 100 | 0 | 0 | na |
| | #2 | 0 | 0 | na | 0 | 0 | na | 6 | 0 | 0 |
| | #3 | 1 | 1 | 100 | 158 | 3 | 2 | 0 | 0 | na |
| pPX100/SL3261 (pUC LT-B) | #1 | 3 | 3 | 100 | 59 | 0 | 0 | 1 | 0 | 0 |
| | #2 | 36 | 0 | 0 | 44 | 0 | 0 | 1 | 0 | 0 |
| | #3 | 360 | 0 | 0 | 0 | 0 | na | 1 | 0 | 0 |
| pGD103/SL3261 (pSC101-derived vector) | #1 | 612 | 612 | 100 | 0 | 0 | na | 8 | 8 | 100 |
| | #2 | 370 | 370 | 100 | 103 | 103 | 100 | 0 | 0 | 100 |
| | #3 | 456 | 456 | 100 | 102 | 102 | 100 | 8 | 8 | 100 |
| pPX3005/SL3261 (pGD103 LT-B) | #1 | 600 | 600 | 100 | 40 | 40 | 100 | 1 | 1 | 100 |
| | #2 | 218 | 218 | 100 | 31 | 31 | 100 | 0 | 0 | na |
| | #3 | 436 | 436 | 100 | 30 | 30 | 100 | 0 | 0 | na |
| 3261λ3 (LT-B integrant) | #1 | 28 | 28 | 100 | 18 | 18 | 100 | 1 | 1 | 100 |
| | #2 | 300 | 300 | 100 | 43 | 43 | 100 | 1 | 1 | 100 |
| | #3 | 480 | 480 | 100 | 29 | 29 | 100 | 1 | 1 | 100 |

Stabilization of Gene Expression in *S. typhi* Vaccine Strains

Although *S. typhimurium* and *S. dublin* attenuated strains may be used to assess immunogenicity in animal models or could be developed into recombinant vaccines for veterinary use, they are not ideally useful in human application to either typhoid fever vaccination programs or as vectors for deliv-

PurA Gene as a Marker for Chromosomal Integration

To create more versatile means to manipulate the *E. coli* purA gene, the 1.74 kilobase pair AccI purA-containing fragment was adapted with various linkers to contain symmetrical unique restriction sites. One linker contained a single restriction site for SalI; the SalI linkered purA gene was cloned into the SalI site of pUC18. This plasmid was subsequently used as a source for the purA gene flanked by unique SalI sites.

A modified transposon was constructed to contain both the purA gene and LT-B (PL controlled) in the following manner. Phage λ112 was first constructed by subcloning the BamHI fragment containing the PL promoter and LT-B structural gene from pPX1602 into a transposition plasmid in which the inverted 31 repeats of Tn10 flanked a kanamycin-resistance determinant. The resulting plasmid, designated pPX1584, contained LT-B and kanamycin-resistance flanked by inverted repeats. The transposable cassette was crossed into a derivative of λgt11 by homologous recombination between the ends of Tn10. The ability of the transposon to yield transposition events was assessed by transducing LB5010/F112. Expression of LT-B was verified in independent isolate. The SalI linkered *E. coli* purA gene was used to replace the kanamycin-resistance determinant of λ112 by directly subcloning the piece into the XhoI site of λ112 and selecting purA+ lysogens in *E. coli* TX595. The modified phage contains purA gene and LT-B and is used to transduce *S. typhimurium* LB5010 ΔpurA/F112 or *S. typhi* aroA ΔpurA/F112 to purine independence. Such transductants invariably arise from the transposition of purA and LT-B to random locations on the Salmonella chromosome.

Strain Deposits

The following strains were deposited with the (ATCC), Rockville, Md., under the provisions of the Budapest Treaty:

| Strain | | ATCC Accession No. | Deposit Date |
| --- | --- | --- | --- |
| S. typhimurium: | BB1231 (aroApurA) | 55107 | October 29, 1990 |
| S. typhimurium: | pPX3005/BB1231 | 68451 | October 29, 1990 |
| S. typhimurium: | pPX3006/BB1231 | 68452 | October 29, 1990 |
| S. typhimurium; | pPX3010/BB1231 | 68453 | October 29, 1990 |
| S. typhimurium: | pPX3009/BB1231 | 68612 | May 3, 1991 |
| S. typhi: | BB1354 | — | May 3, 1991 |

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A plasmid or phage vector which does not contain an antibiotic resistance determinant, which has been additionally modified by the insertion of DNA containing a purA gene encoding adenylosuccinate synthetase.

2. The vector of claim 1 which is a low copy-number plasmid vector.

3. The vector of claim 1 which is a high copy-number plasmid that contains a down regulated purA gene.

4. The vector of claim 1, further comprising a nucleotide sequence encoding at least one antigen or fragment thereof.

5. The vector of claim 4, wherein the antigen is a viral, bacterial, fungal or parasitic antigen of a warm-blooded animal or human pathogen.

6. The vector of claim 5, wherein the bacterial antigen is derived from a pathogen selected from the group consisting of *Haemophilus influenzae, Escherichia coli, Neisseria meningiditis, Streptococcus pneumoniae, Streptococcus pyogenes, Branhamella catarrhalis, Vibrio cholerae, Corynebacterium diphtheriae, Chlamydia trachomatis, Neisseria gonorrhea, Bordetella pertussis, Pseudomonas aeruginosa, Staphylococcus aureus, Klebsiella pneumoniae* and *Clostridium tetani.*

7. The vector of claim 5 wherein the viral antigen is derived from a virus selected from the group consisting of human immunodeficiency virus (types I and II), human T lymphocyte virus (types I, II and III), respiratory syncytial virus, hepatitis A, hepatitis B, hepatitis C, non-A and non-B hepatitis viruses, herpes simplex virus (types I and II), cytomegalovirus, influenza virus, parainfluenza virus, poliovirus, rotavirus, coronavirus, rubella virus, measles virus, varicella virus, Epstein Barr virus, adenovirus, papilloma virus and yellow fever virus.

8. A stable plasmid or phage vector which does not contain an antibiotic resistance locus, the vector containing a purA gene encoding adenylosuccinate synthetase and at least one other gene encoding an antigen or fragment thereof.

9. The vector of claim 8 which is a low copy-number plasmid vector.

10. The vector of claim 8 which is a high copy-number plasmid that contains a down regulated purA gene.

11. The vector of claim 8, wherein the antigen is a viral, bacterial, fungal or parasitic antigen of a warm-blooded animal or human pathogen.

12. A stable low copy-number plasmid vector selected from the group consisting of pPX3005 (ATCC 68451), pPX3006 (ATCC 68452), pPX3009 (ATCC68612), pPX3010 (ATCC 68453) and pPX3007.

13. A purA⁻ bacterial host which harbors the plasmid of claim 1.

14. A purA⁻ bacterial host which harbors the plasmid of claim 8.

15. A purA⁻ attenuated bacterium which harbors a stable plasmid or phage vector, which does not contain an antibiotic resistance determinant, further containing a heterologous purA gene encoding adenylosuccinate synthetase and at least one other gene encoding a heterologous gene product.

16. The bacterium of claim 15, wherein the plasmid is a low copy-number plasmid.

17. The bacterium of claim 15, wherein the plasmid is a high copy-number plasmid that contains a down regulated purA gene.

18. The bacterium of claim 15 which has a purA chromosomal gene mutation and optionally a chromosomal mutation in one or more genes functional in aromatic compound biosynthesis or galactose metabolism.

19. The bacterium of claim 18 in which the optional mutation is an aroA, aroC, aroD, galE mutation or combinations thereof.

20. The bacterium of claim 15, wherein the gene product is of viral, bacterial, fungal or parasitic origin of a warm-blooded or human pathogen.

21. The bacterium of claim 15 which is an enteroinvasive bacterium of the genus Salmonella, Shigella, Yersinia, Escherichia, Vibrio and Campylobacter.

22. A composition comprising a purA⁻ bacterium harboring the plasmid of claim 8.

23. The composition of claim 22, wherein the bacterium is an attenuated enteroinvasive bacterium.

24. The composition of claim 23, wherein the enteroinvasive bacterium is of the genus Salmonella, Shigella, Yersinia, Escherichia, Vibrio, and Campylobacter.

25. The composition of claim 24, wherein the enteroinvasive bacterium is *Salmonella typhi, Salmonella typhimurium* or *Salmonella enteritidis.*

26. The composition of claim 23, in which the bacterium has a purA chromosomal gene mutation and optionally a chromosomal mutation in one or more genes functional in aromatic compound biosynthesis or galactose metabolism.

27. The composition of claim 26 in which the optional mutation is an aroA, aroC, aroD, galE mutation or combinations thereof.

28. The composition of claim 22, wherein the antigen is a viral, bacterial, fungal or parasitic antigen of a warm-blooded animal or human pathogen.

29. The composition of claim 28, wherein the antigen is an epitope of a malarial circumsporozoite protein which is expressed as part of a fusion protein comprising the circumsporozoite epitope and B-subunit of heat-labile enterotoxin of *E. coli* or a portion thereof which combined with the circumsporozoite epitope produces an immunoactive fusion protein.

30. The composition of claim 29, wherein the malaria parasite is *Plasmodium falciparum, Plasmodium vivax, Plasmodium ovale, Plasmodium malariae, Plasmodium berghei, Plasmodium yoelii, Plasmodium knowlesi* and *Plasmodium cynomolgi.*

31. A method for selecting and maintaining bacterial transformants of interest using non-antibiotic selection means, comprising inserting a stable purA vector which does not contain an antibiotic resistance determinant into host bacteria which are deficient in the purA gene, selectively growing the bacteria in adenine-deficient medium and selecting purA plasmid-containing bacterial colonies grown thereon.

32. A plasmid or phage which does not contain an antibiotic resistance determinant, bearing a purA gene whose acquisition by a host cell can be selected by purine-independent growth.

33. A plasmid or phage vector containing a functional partition locus and which does not contain an antibiotic resistance determinant, which has been additionally modified by the insertion of DNA containing the purA gene encoding adenylosuccinate synthetase.

34. The vector of claim 33, wherein the partition locus is parB.

35. A stable plasmid or phage vector which does not contain an antibiotic resistance locus, the vector containing a purA gene encoding adenylosuccinate synthetase, a functional partition loci and at least one other gene encoding an antigen or fragment thereof.

36. The vector of claim 35, wherein the partition locus is parB.

37. A purA$^-$ attenuated bacterium which harbors a stable plasmid which does not contain an antibiotic resistance determinant containing a heterologous purA gene encoding adenylosuccinate synthetase, a functional partition locus and at least one other gene encoding a heterologous gene product.

38. The bacterium of claim 37, wherein the partition locus is parB.

39. A method for selecting and maintaining bacterial transformants of interest using non-antibiotic selection means, comprising inserting a stable purA vector which does not contain an antibiotic resistance determinant into host bacteria containing a functional partition locus and which are deficient in the purA gene, selectively growing the bacteria in adenine-deficient medium, and selecting purA plasmid-containing bacterial colonies grown thereon.

40. The method of claim 39, wherein the partition locus is parB.

41. A stable plasmid or phage vector which does not contain an antibiotic resistance determinant, containing a functional partition locus and bearing a purA gene whose acquisition by a host cell can be selected by purine-independent growth.

\* \* \* \* \*